(12) United States Patent
Huber et al.

(10) Patent No.: US 7,405,212 B2
(45) Date of Patent: Jul. 29, 2008

(54) HELIX MIMETICS AND COMPOSITION AND METHODS RELATED THERETO

(75) Inventors: Vincent Huber, Seattle, WA (US); Jan Urban, San Diego, CA (US); Hiroshi Nakanishi, San Diego, CA (US); Masakatsu Eguchi, Bellevue, WA (US); Jessymol Mathew, Cary, NC (US); Min Sang Lee, Carlsbad, CA (US)

(73) Assignee: Myriad Genetics, Inc., Salt Lake City, UT (US)

( * ) Notice: Subject to any disclaimer, the term of this patent is extended or adjusted under 35 U.S.C. 154(b) by 236 days.

(21) Appl. No.: 11/121,337

(22) Filed: May 3, 2005

(65) Prior Publication Data

US 2005/0222143 A1    Oct. 6, 2005

Related U.S. Application Data

(62) Division of application No. 10/230,974, filed on Aug. 29, 2002, now Pat. No. 6,943,167.

(60) Provisional application No. 60/316,352, filed on Aug. 29, 2001.

(51) Int. Cl.
*C07D 498/08* (2006.01)
*C07D 263/00* (2006.01)

(52) U.S. Cl. .................... 514/234.2; 514/249; 544/145; 544/350

(58) Field of Classification Search ................. 544/145, 544/350; 514/234.2, 249
See application file for complete search history.

(56) References Cited

U.S. PATENT DOCUMENTS 5,446,128 A    8/1995    Kahn et al.
5,710,245 A    1/1998    Kahn et al.
5,840,833 A    11/1998   Kahn et al.
5,859,184 A    1/1999    Kahn et al.

FOREIGN PATENT DOCUMENTS

EP    1130022 A1    9/2001

OTHER PUBLICATIONS

Cook et al. (Chemistry of Penicillin (H. T. Clarke, et al.) (Princeton Univ. Press) (1949) 921-72). Abstract.*
Hodgson et al. (Journal of the American Chemical Society (1954), 76, 1137-40). Abstract.*
Khokhlov et al. (Khimiya Geterotsiklicheskikh Soedinenii (1971), 7(3), 309-15). Abstract.*

* cited by examiner

*Primary Examiner*—Bruck Kifle
(74) *Attorney, Agent, or Firm*—Herbert L. Ley, III; Jay Z. Zhang; Myriad IP Department

(57) ABSTRACT

Compounds which mimic the secondary structure of helical regions of biologically active peptides and proteins having the following structure:

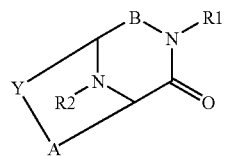

including pharmaceutically acceptable salts and stereoisomers thereof, wherein Y, A, B, $R_1$ and $R_2$ are as defined herein. Such compounds have utility over a wide range of applications, including use as diagnostic and therapeutic agents. In particular, compounds of this invention, and pharmaceutical compositions containing the same, are neurokinin (tachykinin) antagonists. Libraries containing the compounds of this invention are also disclosed, as well as methods for screening such libraries to identify biologically active members.

13 Claims, No Drawings

HELIX MIMETICS AND COMPOSITION AND METHODS RELATED THERETO

CROSS-REFERENCE TO RELATED APPLICATIONS

This is a divisional application of U.S. patent application Ser. No. 10/230,974, filed Aug. 29, 2002 now U.S. Pat. No. 6,943,167, which claims the benefit of U.S. Provisional Patent Application No. 60/316,352, filed Aug. 29, 2001; both of which are incorporated herein by reference in their entirety.

BACKGROUND OF THE INVENTION

1. Field of the Invention

The present invention relates generally to helix mimetics, as well as to compositions and methods related thereto, including chemical libraries of helix mimetics.

2. Description of the Related Art

Proteins are polymers of amino acids in which the carbon atoms and amide groups alternate to form a linear polypeptide, with the amino acid side chains projecting from the α-carbon atom of each amino acid. The sequence of amino acids and location of disulfide bridges (if any) are considered the "primary" protein structure. The "secondary" structure of a protein refers to the steric relationship of amino acid residues that are in close proximity to one another in the linear sequence. Such steric relationships give rise to periodic structure, including the helix. Helices comprise one of three classes of protein secondary structure and display amino acid side chains in a fixed spatial relationship to each other.

The helix is a rod-like structure wherein the polypeptide chain forms the inner part of the rod, and the side chains extend outward in a helical array. The helix is stabilized by hydrogen bonds between the NH and CO groups of the polypeptide chain. The two most common helices, $3_{10}$- and alpha-helices, are found in nature. The latter being the most abundant secondary structure in proteins. More specifically, for $3_{10}$-helix, the hydrogen of the NH group of each amino acid (i.e., amino acid residue "n") is hydrogen bonded to the oxygen of the CO group that is located three amino acid residues behind in the linear polypeptide (i.e., amino acid residue "n-3"). Such hydrogen bonding is illustrated below:

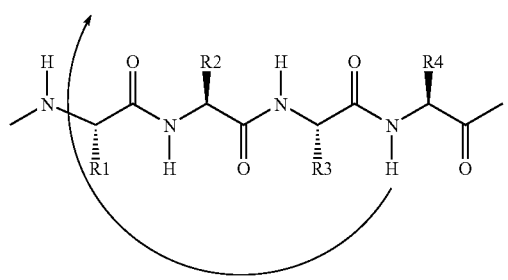

While only a single hydrogen bond is depicted above for purpose of illustration, each of the CO and NH groups of the linear polypeptide are hydrogen bonded in the $3_{10}$-helix. In particular, each amino acid is related to the next by a translation of 2.0 Å along the helix axis and a rotation of 120°, which gives 3 amino acid residues per turn of the $3_{10}$-helix. The pitch of the $3_{10}$-helix is 6.0 Å (the product of the translation, 2.0 Å, and the number of residues per turn, 3), and the radius of the $3_{10}$-helix is 1.9 Å.

For alpha-helix, the most abundant secondary structure in proteins, the hydrogen of the NH group of each amino acid (i.e., amino acid residue "n") is hydrogen bonded to the oxygen of the CO group that is located four amino acid residues behind in the linear polypeptide (i.e., amino acid residue "n-4"). Such hydrogen bonding is illustrated below:

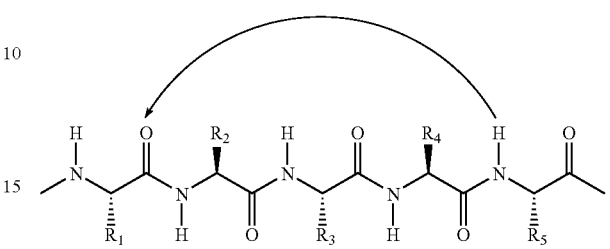

Again, while only a single hydrogen bond is depicted above for purpose of illustration, each of the CO and NH groups of the linear polypeptide are hydrogen bonded in the alpha-helix. In particular, each amino acid is related to the next by a translation of 1.5 Å along the helix axis and a rotation of 100°, which gives 3.6 amino acid residues per turn of the alpha-helix. The pitch of the alpha-helix is 5.4 Å (the product of the translation, 1.5 Å, and the number of residues per turn, 3.6), and the radius of the alpha-helix is 2.3 Å. The "screw sense" of the alpha-helix can be right-handed (clockwise) or left-handed (counter-clockwise). While a few left-handed alpha-helixes do exist, most alpha-helixes found in naturally occurring proteins are right-handed.

In the absence of interactions other than hydrogen-bonding, the alpha-helix is the preferred form of the polypeptide chain since, in this structure, all amino acids are in identical orientation and each forms the same hydrogen bonds. Thus, polyalanine (i.e., $\{-NHCH(CH_3)CO-\}_n$) exists as an alpha-helix. However, the presence of other amino acids within the polypeptide chain may cause instability to the alpha-helix. In other words, the amino acid side chains do not participate in forming the alpha-helix, and may hinder or even prevent alpha-helix formation. A striking example of such side chain dependency on alpha-helix formation is polylysine (i.e., $\{-NHCH((CH_2)_4NH_2)CO-\}_n$). At a pH below 10, the $NH_2$ moiety in the side chain of lysine is charged (i.e., $NH_3^+$), and electrostatic repulsion totally destroys the alpha-helix structure. Conversely, at a pH above 10, the alpha-helix structure is preferred.

The helix constitutes one of the principle architectural features of peptides and proteins, and are important structural elements in a number of biological recognition events, including ligand-receptor interactions, protein-DNA interactions, protein-RNA interactions, and protein-membrane interactions. A number of alpha-helix mimetics have been developed to stabilize the alpha-helical structure of a natural or synthetic peptide or protein, particularly the secondary structure of helices. For example, U.S. Pat. Nos. 5,446,128, and 5,710,245 disclose compounds that initiate and stabilize the three-dimensional structure of the helix, while U.S. Pat. Nos. 5,840,833 and 5,859,184 disclose compounds with covalent bonds linking the inner core or backbone of the helix, and thus stabilize the three-dimensional structure of the helix.

In view of the important biological role played by the helix, there is a need in the art for compounds that can mimic the helix structure. There is also a need in the art for methods of making stable helix mimetics, as well as the use of such stabilized structures to effect or modify biological recognition events which involve helical structures. The present invention fulfills these needs and provides further related advantages.

SUMMARY OF THE INVENTION

In brief, the present invention is directed to conformationally constrained compounds which mimic the secondary structure of helical regions of biologically active peptides and proteins (also referred to herein as "helix mimetics"). The compounds of the present invention may generally be characterized as "fused bicyclo compounds" and have the following general structure (I):

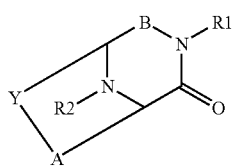

including pharmaceutically acceptable salts and stereoisomers thereof, wherein A, B, Y, $R_1$ and $R_2$ are as defined below.

The present invention is also directed to libraries containing compounds of structure (I), as well as methods for synthesizing such libraries and methods for screening the same to identify biologically active compounds. In addition, compositions containing a compound of this invention in combination with a pharmaceutically acceptable carrier are disclosed. Methods for treatment and/or prevention of central nervous system disorders, as well as other disorders, with the compounds and compositions of this invention are also disclosed.

These and other aspects of this invention will be apparent upon reference to the following detailed description. To this end, various references are set forth herein which describe in more detail certain procedures, compounds and/or compositions, and are incorporated by reference in their entirety.

DETAILED DESCRIPTION OF THE INVENTION

The present invention is generally directed to helix mimetics. The helix mimetics of the present invention are useful as bioactive agents, including (but not limited to) use as diagnostic, prophylactic and/or therapeutic agents for central nervous system disorders, as well as other disorders as discussed herein. Chemical libraries of helix mimetics, which are useful in the identification of bioactive agents, are also disclosed. In the practice of the present invention, the libraries may contain from tens to hundreds to thousands (or greater) of individual helix mimetics (also referred to herein as "members").

In one aspect of the present invention, compounds are disclosed that mimic the secondary structure of helical regions of biologically active peptides and proteins (also referred to herein as "helix mimetics"). Such compounds may generally be referred to as having "fused bicyclo compounds" since two carbon atoms (separated by a nitrogen atom) serve as the bridging atoms for two fused rings. More particularly, the fused bicyclo compounds of this invention have the following structure (I):

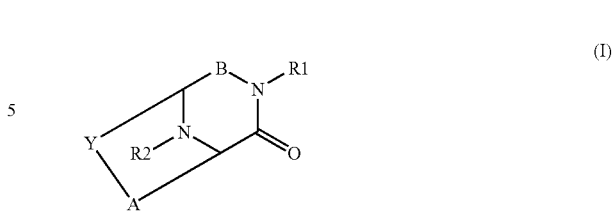

or a pharmaceutically acceptable salt or stereoisomer thereof, wherein

Y is —N($R_3$)C(=O)—, —N($R_3$)—, —OC(=O)—, —O—, —$SO_2$—, —SO— or —S—;

A is —($CR_4R_{4a}$)$_m$—;

B is —($CR_5R_{5a}$)$_n$—;

m is 1, 2, 3 or 4 when Y is —N($R_3$)—, —O—, —$SO_2$—, —SO— or —S—;

m is 1, 2 or 3 when Y is —N($R_3$)C(=O)— or —OC(=O)—;

n is 1, 2, or 3;

$R_4$ and $R_5$ are, at each occurrence, the same or different and independently an amino acid side chain moiety or an amino acid side chain derivative;

$R_{4a}$ and $R_{5a}$ are, at each occurrence, the same or different and independently hydrogen, hydroxy, —COOH, —$CONH_2$, —$R_6$, —$OR_6$, —$COOR_6$, —$COR_6$ or —$CONHR_6$;

$R_6$ is a lower alkyl optionally substituted with halogen or hydroxy;

$R_2$ is -Z-(amino acid side chain moiety) or -Z-(amino acid side chain derivative), where Z is a direct bond or —C(=O)—, —C(=O)O—, —C(=O)NH—, —C(=NH)—, —$SO_2$— or —P(O)$_{2,3}$—; and $R_1$ and $R_3$ are the same or different and represent the remainder of the molecule;

wherein any two adjacent CH groups (i.e., CH—CH) or adjacent NH and CH groups (i.e., NH—CH) of the fused bicyclo compound optionally form a double bond (i.e., C=C or N=C, respectively);

and with the provisos that:

(a) when Y is —S— or —SO—, $R_1$ is not hydrogen; and (b) when Y is —S— and m is 1, $R_4$ and $R_{4a}$ are not both methyl when $R_1$ is —C(=O)W, where W is phenyl, benzyl, —$CH_2$O(phenyl) or —OC(=O)(benzyl).

As used herein, an "amino acid side chain moiety" refers to any amino acid side chain moiety present in naturally occurring alpha-amino acids and other "non-protein" amino acids. "Non-protein" amino acids refer to alpha-amino acids, beta-amino acids and gamma-amino acids which are not naturally occurring, but which are commonly utilized by those in the field of peptide chemistry when preparing synthetic analogues of naturally occurring peptides, including D and L forms. An "amino acid side chain moiety" as used herein, includes (but is not limited to) the naturally occurring amino acid side chain moieties identified in Table 1 below. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine, phosphothreonine and phosphoserine. In addition, glycosylated amino acid side chains may also be used in the practice of this invention, including (but not limited to) glycosylated threonine, serine, glutamine and asparagine.

TABLE 1

Naturally Occurring Amino Acid Side Chain Moieties

| Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_2$ | Lysine |
| —(CH$_2$)$_3$NHC(NH$_2$)NH$_2$ | Arginine |
| 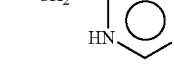 | Histidine |
| —CH$_2$COOH | Aspartic acid |
| —CH$_2$CH$_2$COOH | Glutamic acid |
| —CH$_2$CONH$_2$ | Asparagine |
| —CH$_2$CH$_2$CONH$_2$ | Glutamine |
| 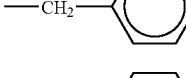 | Phenylalanine |
|  | Tyrosine |
| 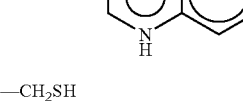 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 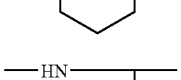 | Proline |
| 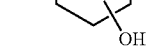 | Hydroxyproline |

In addition, as used herein, an "amino acid side chain derivative" represents modifications and/or variations to amino acid side chain moieties. For example, the amino acid side chain moieties of alanine, valine, leucine, isoleucine and phenylalanine may generally be classified as alkyl, aryl or arylalkyl moieties, optionally substituted with one or more substituents as defined below. Accordingly, representative amino acid side chain derivatives include substituted or unsubstituted alkyl, aryl, arylalkyl, heterocycle, heterocyclealkyl, heteroaryl and heteroarylalkyl moieties.

Examples of amino acid side chain derivatives include (but are not limited to) hydroxylysine, homoserine, homotyrosine, homophenylalanine, citrulline, kynurenine, 4-aminophenylalanine, 3-(2-naphthyl)-alanine, 3-(1-naphthyl) alanine, methionine sulfone, t-butyl-alanine, t-butylglycine, 4-hydroxyphenylglycine, aminoalanine, phenylglycine, vinylalanine, prop argyl-glycine, 1,2,4-triazolo-3-alanine, 4,4,4-trifluoro-threonine, thyronine, 6-hydroxytryptophan, 5-hydroxytryptophan, 3-hydroxykynurenine, 3-aminotyrosine, trifuoromethyl-alanine, 2-thienylalanine, (2-(4-pyridyl) ethyl)cysteine, 3,4-dimethoxy-phenylalanine, 3,5-bistrifluoro-phenylalanine,3-(2-thiazolyl)-alanine, ibotenic acid, 1-amino-1cyclopentane-carboxylic acid, 1-amino-1cyclohexanecarboxylic acid, quisqualic acid, 3-trifluoromethylphenylalanine, 4-trifluoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of the following: a (C$_1$-C$_4$) alkyl, a (C$_1$-C$_4$) alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl)alanine, β-(1 and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine and δ-alkyl ornithine, and the like. Any of these "amino acid side chain derivative" maybe substituted with a methyl group at the alpha, beta or gamma positions, a halogen at any aromatic residue on the amino side chain, or an appropriate protective group at the O, N, or S atoms of the side chain moieties. Appropriate protective groups are disclosed in "Protective Groups In Organic Synthesis," T. W. Greene and P. G. M. Wuts, J. Wiley & Sons, NY, MY, 1991.

To this end, the term "alkyl" is a straight chain or branched, cyclic or noncyclic, saturated or unsaturated alkyl containing from 1 to 12 carbon atoms (also referred to herein as "C$_{1-12}$alkyl"). Similarly, a "lower alkyl" is as defined above, but contains from 1 to 4 carbon atoms (also referred to herein as a "C$_{1-4}$alkyl"). Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative unsaturated cyclic alkyls include cyclopentenyl and cyclohexenyl, and the like.

"Aryl" is an aromatic carbocyclic moiety contain from 6 to 12 carbon atoms (also referred to herein as a "C$_{6-12}$aryl"), such as phenyl and naphthyl.

"Arylalkyl" is an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

Similarly, the amino acid side chain moieties of histidine, tryptophan, proline and hydroxyproline may generally be classified as heterocyclie or heterocyclecalkyl moieties, optionally substituted with one or more substituents as defined below. Accordingly, representative amino acid side chain derivatives also include substituted or unsubstituted heterocycle and heterocyclealkyl moieties.

As used herein, "heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle moiety, such as —$CH_2$(heterocycle), —$(CH_2)_2$(heterocycle), and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, and the like.

"Heteroarylalkyl" means an alkyl having at least one alkyl hydrogen atom replaced with a heteroaryl moiety, such as —$CH_2$pyridinyl, —$CH_2$pyrimidinyl, and the like.

The term "substituted" as used herein means any of the above groups—that is, alkyl, aryl, arylalkyl, heterocycle, heterocyclealkyl, heteroaryl or heteroarylalkyl—wherein at least one hydrogen atom is replaced with a substituent. In the case of an oxo substituent ("=O"), two hydrogen atoms are replaced. A "substituent" in this regard is halogen, oxo, hydroxy, haloalkyl (such as trifluoromethyl), —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —$SO_2$R, —$NRSO_2$R, —Si(R)$_3$, or —OP(OR)$_3$, wherein each occurrence of R is the same or different and independently hydrogen, alkyl, substituted alkyl, aryl, substituted aryl, arylalkyl, substituted arylalkyl, heterocycle, substituted heterocycle, heterocyclealkyl or substituted heterocyclealkyl, or wherein any two R groups attached to the same nitrogen atom, taken together with the nitrogen atom to which they are attached, form a heterocycle or a substituted heterocycle.

A "peptide" means at least two naturally occurring amino acids joined via a peptide bond. Depending upon the number of amino acids joined via peptide bonds, the resulting peptide may also be referred to as a "polypeptide" or "protein." Similarly, a "peptide derivative" means a peptide which has been covalently modified and/or which contains amino acids other than alpha-amino acids. Representative peptide derivatives include peptides which are N-alkylated, N-acylated or N-sulfonylated at the amino termini, with, for example, methyl, benzyl, acetyl, benzoyl, methanesulfonyl, phenylsulfonyl, allyloxycarbonyl, t-butyloxycarbonyl, benzyloxycarbonyl, or fluorenyloxycarbonyl moieties; peptides in which the carboxy termini are esterified (methyl, ethyl, benzyl) or reduced to a hydroxy or aldehyde; peptides which are N-alkylated at peptide bonds with, for example, methyl or 2-hydroxy-4-methoxybenzyl; and peptides which incorporate beta- or gamma-amino acids such as beta-alanine or gamma-aminobutyric acid.

A "linker" is any covalent bridging moiety that facilitates linkage of a compound of structure (I), through the respective $R_1$, $R_2$, $R_3$, $R_4$, $R_{4a}$, $R_5$ and/or $R_{5a}$ moiety, to another moiety, agent, compound, solid support, molecule, amino acid, peptide or protein. For example, the compounds of this invention may be linked to one or more known compounds, such as biotin, for use in diagnostic or screening assays. Furthermore, one (or more) of $R_1$, $R_2$, $R_3$, $R_4$, $R_{4a}$, $R_5$ or $R_{5a}$ may be a linker joining the compound of structure (I) to a solid support (such as a support used in solid phase peptide synthesis). Examples of such linkers include p-alkoxybenzyl alcohol, phenylacetamidomethyl, and 2-chlorotrityl chloride. In one example, linkage to another moiety or compound, or to a solid support, is at the $R_1$ or $R_3$ position.

A "solid support" means any composition of matter to which another compound is attached directly or attached through a linker and which is insoluble in at least one solvent that the attached compound is soluble in. Alternatively, a "solid support" may be a composition of matter with similar solubility characteristics to the attached compound, but which may be readily precipitated from solution and filtered off as a solid. Representative examples include polystyrene, polyethylene glycol, polystyrene grafted with polyethylene glycol, polyacrylamide, polyamide-polyethylene glycol copolymer, controlled-pore glass, and silica.

The phrase "remainder of the molecule" means any moiety, agent, compound, solid support, molecule, linker, amino acid, peptide or protein covalently attached to the helix mimetic at either the $R_1$ and/or $R_3$ positions, including amino acid side chain moieties, amino acid side chain derivatives and peptide derivatives as defined above, as well as moieties such as -Z-(amino acid side chain moiety) and -Z-(amino acid side chain derivative) where Z is as defined above in the context of the $R_2$ moiety. Accordingly, an alternative depiction of structure (I), the bond between the ring nitrogen atoms and the corresponding $R_1$ and $R_3$ moieties may be left undefined, as represented by the following structure (I') when Y is —N($R_3$)— or —N($R_3$)C(=O)—, and by the following structure (I") when Y is —O—, —OC(=O)—, —$SO_2$—, —SO—, or —S—:

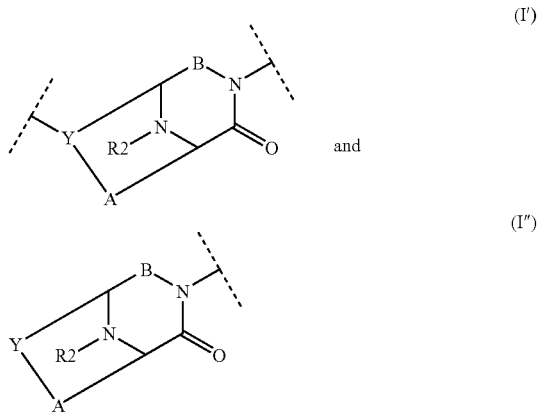

wherein "- - - -" represents the remainder of the molecule joined to the corresponding ring nitrogen through a covalent bond, and A, B, Y and $R_2$ are as defined above.

With regard to stereoisomers, it should be understood that a solid line designation in Structure (I) for attachment of an R group to a chiral atom of the fused bicyclo rings indicates that these groups may lie either below or above the plane of the page (i.e., "····R" or "——R"). All isomeric forms of the compounds of Structure (I) are included within the present invention, including racemates, rauemic mixtures and individual enantiomers or diasteromers. For example, the compounds of this invention have the stereoconformation of structure (Ia) when intended to mimic a helix of L-form amino acids, and structure (Ib) when intended to mimic a helix of D-form amino acids:

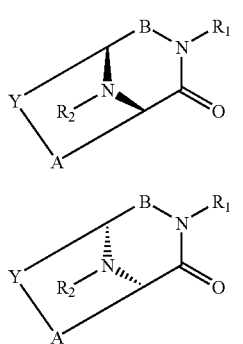

The term "pharmaceutically acceptable salt" is intended to encompass any and all acceptable salt forms of the compounds of Structure (I). For example, the compounds of this invention may generally be utilized as the free acid or free base, or used in the form of acid or base addition salts, which addition salts are well known to those skilled in the pharmaceutical or formulation field.

In a first embodiment of structure (I), Y is —N(R$_3$)C(=O)— and the compounds of this invention have the following structure (II):

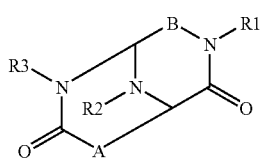

including pharmaceutically acceptable salts and stereoisomers thereof, wherein A, B, R$_1$, R$_2$ and R$_3$ are as defined above.

In a more specific embodiment of structure (II), all occurrence of R$_4$, R$_{4a}$, R$_5$ and R$_{5a}$ are hydrogen, and the compounds of this invention have the following structure (II'):

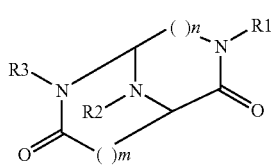

including pharmaceutically acceptable salts and stereoisomers thereof, wherein m, n, R$_1$, R$_2$ and R$_3$ are as defined above.

In a more specific embodiment of structure (II'), m is 1, n is 1, and the compounds of this invention have the following structure (II"):

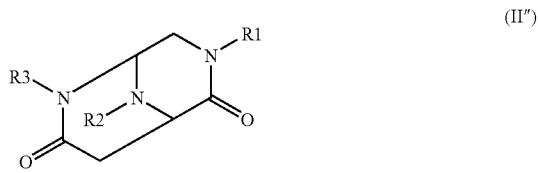

including pharmaceutically acceptable salts and stereoisomers thereof, wherein R$_1$, R$_2$ and R$_3$ are as defined above.

In a more specific embodiment of structure (II"), R$_1$ and R$_3$ are the same or different and independently an amino acid side chain moiety or amino acid side chain derivative, R$_2$ is —C(=O)R$_7$, —C(=O)OR$_7$, —C(=O)NHR$_7$ or —SO$_2$R$_7$, where R$_7$ is an amino acid side chain moiety or an amino acid side chain derivative. In a still more specific embodiment, R$_7$ is aryl, arylalkyl, heterocycle, heterocyclealkyl or heteroarylalkyl optionally and independently substituted with one or more halogen, —CF$_3$, —COOH, —NH$_2$, —OH or —NO$_2$. In a still further embodiment, R$_7$ is alkyl or substituted alkyl. In a still further embodiment, R$_7$ is substituted alkyl having the following structure —(CH$_2$)$_p$—NH$_2$ or —(CH$_2$)$_p$—N(R')$_2$, where p is 2-6 and R' is independently hydrogen, alkyl or heterocycle.

In a second embodiment of structure (I), Y is —N(R$_3$)— and the compounds of this invention have the following structure (III):

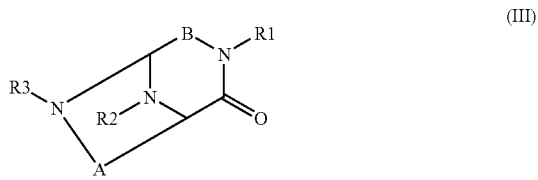

including pharmaceutically acceptable salts and stereoisomers thereof, wherein A, B, R$_1$, R$_2$ and R$_3$ are as defined above.

In a more specific the embodiment of structure (III), all occurrence of R$_4$, R$_{4a}$, R$_5$ and R$_{5a}$ are hydrogen, and the compounds of this invention have the following structure (III'):

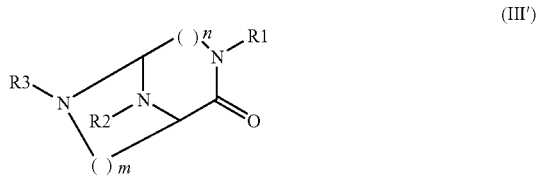

including pharmaceutically acceptable salts and stereoisomers thereof, wherein m, n, R$_1$, R$_2$ and R$_3$ are as defined above.

In a more specific the embodiment of structure (III'), m is 2 and n is 1, and the compound of this invention have the following structure (III"):

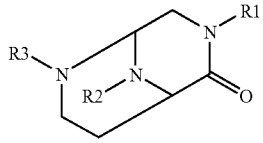

(III")

including pharmaceutically acceptable salts and stereoisomers thereof, wherein $R_1$, $R_2$ and $R_3$ are as defined above.

In a still more specific embodiment of structure (III"), including pharmaceutically acceptable salts and stereoisomers thereof, $R_1$ is amino acid side chain moiety or amino acid side chain derivative, $R_2$ and $R_3$ are the same or different and independently —C(═O)—$R_7$, —C(═O)O$R_7$, —CNH$R_7$ or —SO$_2$—$R_7$, where $R_7$ is an amino acid side chain moiety or an amino acid side chain derivative. In a still more specific embodiment of structure, $R_7$ is aryl, arylalkyl, heterocycle, heterocyclealkyl or heteroarylalkyl optionally and independently substituted with one or more halogen, —CF$_3$, —COOH, —NH$_2$, —OH or —NO$_2$. In a still further embodiment of structure, $R_7$ is alkyl or substituted alkyl. In a still further embodiment, $R_7$ is substituted alkyl having the following structure —(CH$_2$)$_p$—NH$_2$ or —(CH$_2$)$_p$—N(R')$_2$, where p is 2-6 and R' is independently hydrogen, alkyl or heterocycle.

In a third embodiment of structure (I), Y is —OC(═O)—, and the compounds of this invention have the following structure (IV):

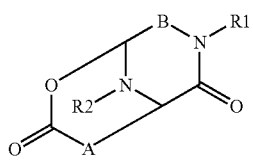

(IV)

including pharmaceutically acceptable salts and stereoisomers thereof, wherein A, B, $R_1$, and $R_2$ are as defined above.

In a more specific embodiment of structure (IV), all occurrence of $R_4$, $R_{4a}$, $R_5$ and $R_{5a}$ are hydrogen, and the compounds of this invention have the following structure (IV'):

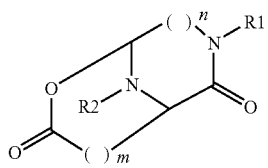

(IV')

including pharmaceutically acceptable salts and stereoisomers thereof, wherein m, n, $R_1$ and $R_2$ are as defined above.

In still a more specific embodiment of structure (IV'), m is 1, n is 1 and the compounds of this invention have the following structure (IV"):

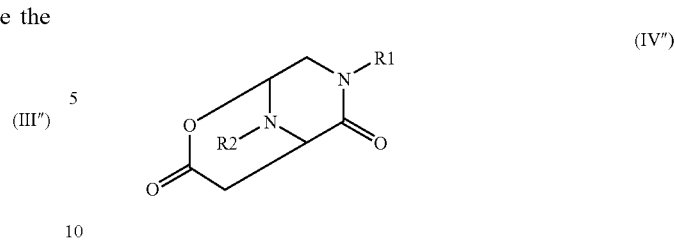

(IV")

including pharmaceutically acceptable salts and stereoisomers thereof, wherein $R_1$ and $R_2$ are as defined above.

In a fourth embodiment of structure (I), Y is —O—, the compounds of this invention have the following structure (V):

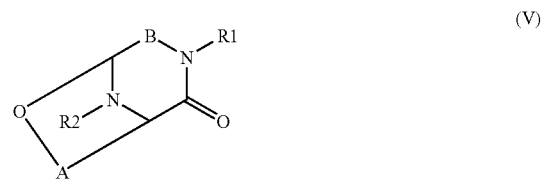

(V)

including pharmaceutically acceptable salts and stereoisomers thereof, wherein A, B, $R_1$, and $R_2$ are as defined above.

In a more specific embodiment of structure (V), all occurrence of $R_4$, $R_{4a}$, $R_5$ and $R_{5a}$ are hydrogen, and the compounds of this invention have the following structure (V'):

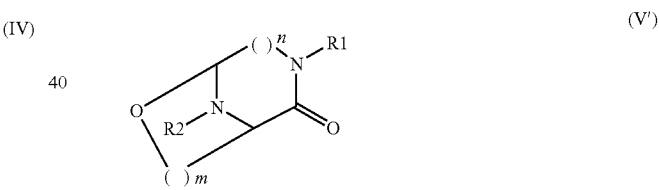

(V')

including pharmaceutically acceptable salts and stereoisomers thereof, wherein m, n, $R_1$, and $R_2$ are as defined above.

In a more specific embodiment of structure (V'), m is 1, n is 1 and the compounds of this invention have the following structure (V"):

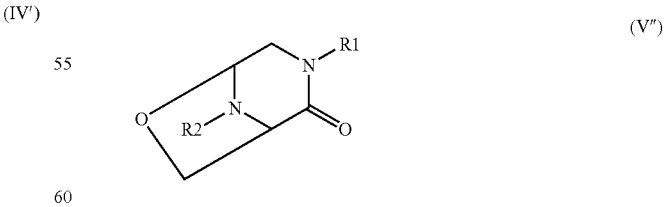

(V")

including pharmaceutically acceptable salts and stereoisomers thereof, wherein $R_1$ and $R_2$ are as defined above.

In a fifth embodiment of structure (I), Y is —SO$_2$—, the compounds of this invention have the following structure (VI):

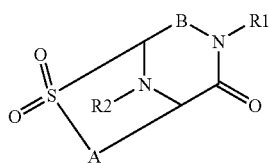

(VI)

including pharmaceutically acceptable salts and stereoisomers thereof, wherein A, B, $R_1$, and $R_2$ are as defined above.

In a more specific embodiment of structure (VI), all occurrences of $R_4$, $R_{4a}$, $R_5$ and $R_{5a}$ are hydrogen, and the compounds of this invention have the following structure (VI'):

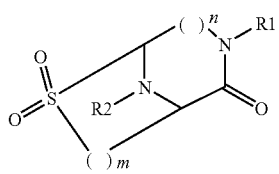

(VI')

including pharmaceutically acceptable salts and stereoisomers thereof, wherein m, n, $R_1$, and $R_2$ are as defined above.

In a more specific embodiment of structure (VI'), m is 1, n is 1 and the compounds of this invention have the following structure (VI"):

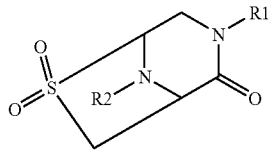

(VI")

including pharmaceutically acceptable salts and stereoisomers thereof, wherein $R_1$ and $R_2$ are as defined above.

In a sixth embodiment of structure (I), Y is —SO—, the compounds of this invention have the following structure (VII):

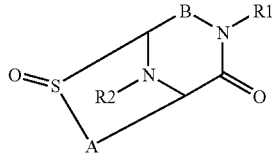

(VII)

including pharmaceutically acceptable salts and stereoisomers thereof, wherein A, B, $R_1$, and $R_2$ are as defined above.

In a more specific embodiment of structure (VII), all occurrences of $R_4$, $R_{4a}$, $R_5$ and $R_{5a}$ are hydrogen, and the compounds of this invention have the following structure (VII'):

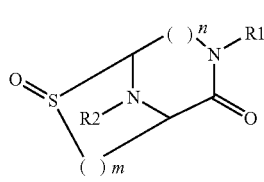

(VII')

including pharmaceutically acceptable salts and stereoisomers thereof, wherein m, n, $R_1$, and $R_2$ are as defined above.

In a more specific embodiment of structure (VII'), m is 1, n is 1 and the compounds of this invention have the following structure (VII"):

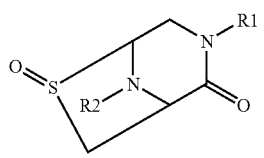

(VII")

including pharmaceutically acceptable salts and stereoisomers thereof, wherein $R_1$ and $R_2$ are as defined above.

In a seventh embodiment structure (I), Y is —S—, the compounds of this invention have the following structure (VIII):

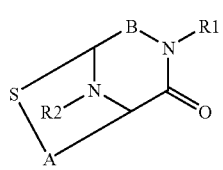

(VIII)

including pharmaceutically acceptable salts and stereoisomers thereof, wherein A, B, $R_1$ and $R_2$ are as defined above.

In a more specific embodiment of structure (VIII), all occurrence of $R_4$, $R_{4a}$, $R_5$ and $R_{5a}$ are hydrogen, and the compound of this invention have the following structure (VIII'):

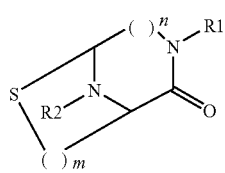

(VIII')

including pharmaceutically acceptable salts and stereoisomers thereof, wherein m, n, $R_1$ and $R_2$ are as defined above.

In a more specific embodiment of structure (VIII'), m is 1, n is 1 and the compound of this invention have the following structure (VIII"):

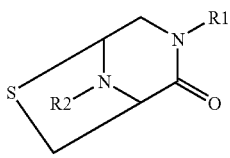

(VIII″)

including pharmaceutically acceptable salts and stereoisomers thereof, wherein $R_1$ and $R_2$ are as defined above.

As mentioned above, the helix mimetics of the present invention are useful as bio-active agents, such as diagnostic, prophylactic, and therapeutic agents. The helix mimetics were found to effectively displace substance P in a calcium flux assay. The data thus indicate the ability of helix mimetics to antagonize neurokinin-1 and serve as potential therapy for central nervous system disorders and other disorders.

In this invention, libraries containing helix mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest are referred to herein as "bioactive library members" or "bioactive mimetics." For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields helix mimetics which are themselves biologically active, and thus useful as diagnostic, prophylactic or therapeutic agents, and may further be used to significantly advance identification of lead compounds in these fields.

Synthesis of the helix mimetics of the library of the present invention may be accomplished using known peptide synthesis techniques, in combination with the component pieces of this invention. More specifically, any amino acid sequence may be added as any of the $R_1$, $R_2$, $R_3$, $R_4$, $R_4$, $R_5$ or $R_{5a}$ moieties of the helix mimetic. Preferably the amino acid sequence may be added as the $R_1$ or $R_3$ moieties. To this end, the mimetics may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis*, 1984, Pierce Chemical Comp., Rockford, Ill.; Atherton, E., Shepard, R. C. *Solid Phase Peptide Synthesis: A Practical Approach*; IRL: Oxford, 1989) or on a silyl-linked resin by alcohol attachment (Randolph et al., *J. Am. Chem. Soc.* 117:5712-14, 1995). The utility and ease of synthesis of the helix mimetic of the present invention is further exemplified by the applicability of wide variety of commercially available resins. To this end, core of either polystyrene or ArgoGel (polyethyleneglycol grafted polystyrene; Argonaut, San Carlos, Calif.) utilizing aminomethyl polystyrene, benzhydrylamine (BHA) methylbenzhydrylamine (MBHA) (Matsueda et al., *Peptides* 2:45, 1981), phenoxybenzylalcohol (Wang resin) (Wang *J. Am. Chem. Soc.* 95:1328, 1973), 2-clorotrytyl (Barlos et al., *Tetrahedron Lett.* 30:3943, 1989, ibid 30:3947, 1989), and PAL (Albericio et al., *J. Org. Chem.* 55:3730 1990) resins and other resins could be used in the synthesis of the present invention.

In addition, a combination of both solution and solid phase synthesis techniques may be utilized to synthesize the helix mimetics of this invention. For example, a solid support may be utilized to synthesize the linear peptide sequence up to the point that the helix mimetic is added to the sequence. A suitable conformationally constrained helix mimetic which has been previously synthesized by solution synthesis techniques may then be added as the next "amino acid" to the solid phase synthesis (i.e., the helix mimetic, which has at least two reactive sites, may be utilized as the next residue to be added to the linear peptide). Upon incorporation of the helix mimetic into the sequence, additional amino acids may then be added to complete the peptide bound to the solid support. Alternatively, the linear N-terminus and C-terminus protected peptide sequences may be synthesized on a solid support, removed from the support, and then coupled to the helix mimetic in solution using known solution coupling techniques.

In this regard, the helix mimetics of the present invention may generally be prepared by sequential coupling of the individual component pieces either stepwise in solution or by solid phase synthesis illustrated in the following General Reaction Scheme. Such techniques are further illustrated in the Examples.

General Reaction Scheme

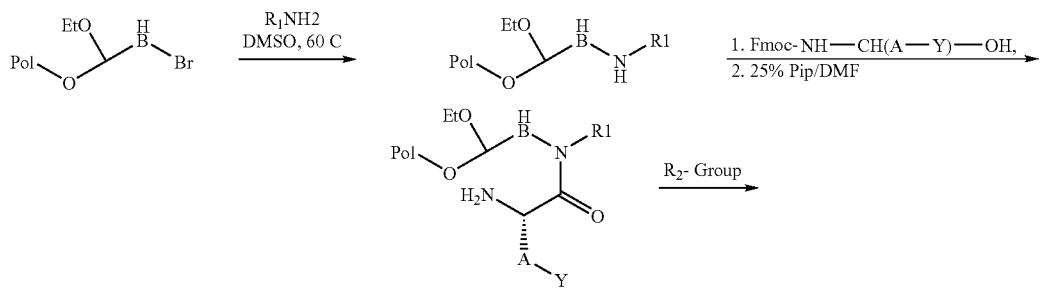

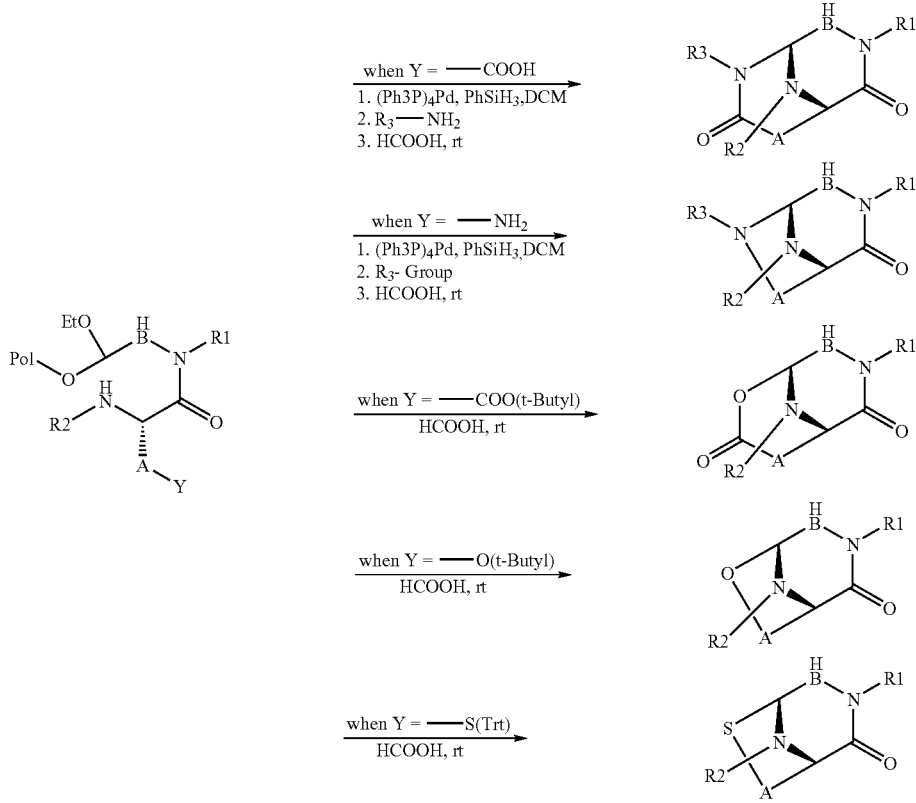

In another aspect of this invention, methods for constructing libraries are disclosed. Traditional combinatorial chemistry (e.g., *The Combinatorial Index* Bunin, Academic Press, New York, 1998; Gallop et al., *J. Med. Chem.* 37:1233-1251, 1994) and parallel synthesis techniques permit a vast number of compounds to be rapidly prepared by the sequential combination of reagents to a basic molecular scaffold. For example, the above disclosed synthesis may be carried out using the directed sorting technique of Nicolaou and coworkers. (Nicolaou et al., Angew. *Chem. Int'l. Ed.* 34:2289-2291, 1995). Presently, equipment for this technique is commercially available from IRORI (La Jolla, Calif.). Alternatively, the above disclosed synthesis may be carried out by parallel synthesis using a 48- or 96-well plate format wherein each well contains a fritted outlet for draining solvents and reagents (*A Practical Guide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the calorimetric assay disclosed by Lam et al. (*Nature* 354:82-84, 1991) or Griminski et al. (*Biotechnology* 12:1008-1011, 1994). In a preferred embodiment, the library members are in solution and the target is immobilized on a solid phase. Alternatively, the library may be immobilized on a solid phase and may be probed by contacting it with the target in solution.

In another aspect, the present invention encompasses pharmaceutical compositions prepared for storage or administration which comprise a therapeutically effective amount of a compound of the present invention in a pharmaceutically acceptable carrier or diluent. The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors, which those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceutical Sciences*, Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compounds of the present invention are useful in the prevention and treatment of a wide variety of clinical conditions which are characterized by the presence of an excess tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, or example AIDS related neuropathy, diabetic neuropathy, chemotherapy-induced neuropathy, and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such eczema and rhinitis; hyper sensitivity disorders such as poison ivy; ophthalmic diseases such a conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; postoperative neuroma, particularly of mastectomy; vulvar vestibulitis; amniogenesis; adverse immunological reactions such as rejection of transplanted tissues and disorders related to immune enhancement of suppression, such as systemic lupus erythmatosus; gastrointestinal (GI) disorders, including inflammatory disorders, and disease of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain of nociception, for example, chronic pain of that attributable to or associated with any of the foregoing conditions especially the transmission of pain in migraine, of such as headache, toothache, cancerous pain, back pain, and superficial pain on congelation, burn, herpes zoster of diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, this compounds is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for example, by D. J. Stewart in "Nausea and Vomiting: Recent Research and Clinical Advances," Eds. J. Kucharczyk et al., CRC Press Inc., Boca Raton, Fla., USA (1991), pages 177-203. Commonly used chemotherapeutic agents include cisplatin, dacarbazine, mechlorethamine, streptozocin, cyclophosphamide, carmustine, lomustine, doxorubicin, daunorubicin, procarbazine, mitomycin, cytarabine, etoposide, methotrexate, 5-fluorouracil, vinblastine, vincristine, bleomycin, and chlorambucil (Gralla et al., *Cancer Treatment Reports* 68, 163-172, 1984).

The compounds of the present invention are also of use in the treatment of emesis induced by radiation including radiation therapy such as in the treatment of cancer, or radiation sickness, and in the treatment of post-operative nausea and vomiting.

Further, the compounds of the present invention can act as calcium channel blocking agents. As such, the compounds of the present invention are useful in the prevention or treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrug resistance in tumor cells by enhancing the efficacy of chemotherapeutic agents. In addition, the compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; asthma; osteoarthritis; rheumatoid arthritis; and migraine. The compounds of the present invention are also particularly useful in the treatment of diseases characterized by neurogenic mucus secretion, especially cystic fibrosis.

The compounds of this invention may be administered by inhalation, and thus may be delivered in the form of an aerosol spray from pressurized packs or nebulizers. The compounds may also be delivered as powders which may be formulated and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compound molecules are coupled. The neurokinin inhibitors may also be coupled with soluble polymers as targetable drug carriers. Such polymers can include polyvinylpyrrolidone, pyran copolymer, polyhydroxy-propyl-methacrylamide-phenol, polyhydroxyethyl-aspartarnide-phenol, or polyethyleneoxide-polylysine substituted with palmitoyl residues. Furthermore, the neurokinin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of this invention may be used in the form of a pharmaceutical preparation, for example in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparation, in solid, semisolid, or liquid form, and in addition auxiliary, stabilizing, thickening and coloring agents and perfumes may be used. The active object compounds is included in the pharmaceutical composition in an amount sufficient to produce the desired effect upon the process or condition of the disease.

For preparing solid compositions such as tablets, the principal active ingredient is mixed with a pharmaceutical carrier; conventional tableting ingredients such as corn starch, lactose, sucrose, sorbitol, talc, stearic acid, magnesium stearate, dicalcium phosphate or gums, and other pharmaceutical diluents; water, to from a solid preformulation composition containing homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type, described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers coatings, such materials including a number of polymeric acids and mixtures of polymeric acids with such materials as shellac, acetyl alcohol and cellulose acetate.

The liquid forms in which the compositions of the present invention may be incorporated for administration orally or by injection include aqueous solution, suitably flavored syrups, aqueous or oil suspensions, and emulsions with acceptable oils such as cottonseed oil, sesame oil, coconut oil or peanut oil, or with solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent. For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

Similarly, for the treatment of respiratory diseases, such as asthma, a compound of the present invention may be used in conjunction with a bronchodilator, such as a $\beta_2$-adrenergic receptor agonist of a tachykinin antagonist which acts at neurokinin-2 receptors. Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, a compound of the present invention may be used in conjunction with a tachykinin antagonist which acts at neurokinin-2 receptors, or with tachykinin receptor antagonist which acts at neurokinin-1, neurokinin-2, and neurokinin-3 receptors. Similarly, for the prevention of treatment of emesis a compound of the present invention may be used in conjunction with other anti-emetic agents, especially $5HT_3$ receptor antagonists, such as ondansetron, granisetron, tropisetron, decadron, zatisetron, as well as other commercially and naturally available pharmacologically active agents. Likewise, for the prevention or treatment of migraine a compound of the present invention may be used in conjunction with other anti-migraine agents, such as ergotamines or $5HT_3$ agonists, especially sumatriptan. Likewise, for the treatment of behavioral hyperalgesia, a compound of the present invention may be used in conjunction with an antagonist of N-methyl D-asparatate (NMDA), such as dizocilpine. For the prevention of treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication of special diets then being followed by patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to about 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to about 25 mg/kg per day, preferably about 0.05 to about 10 mg/kg per day, and especially about 0.1 to about 5 mg/kg per day. A compound may be administered on a regimen of 1 to 4 times per day, preferably once or twice per day. In the treatment of emesis using an injectable formulation, a suitable dosage level is about 0.001 to about 10 mg/kg per day, preferably about 0.005 to about 5 mg/kg per day, and especially about 0.05 to about 5 mg/kg per day. A compound may be administered on a regiment of 1 to 4 times per day, preferably once or twice per day.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

The following examples are provided for purposes of illustration, not limitation. These examples illustrate the syntheses of helix mimetics of this invention. Specifically, the preparation of helix mimetics was carried out on solid phase. The solid phase syntheses of these helix mimetics demonstrate that libraries containing such members may be readily prepared.

TABLE 2

| Abbreviations used in Examples | |
|---|---|
| Reagents: | |
| AcOH | acetic acid |
| BOP | benzotriazol-1-yloxy-tris(dimethylamino)phosphonium hexafluorophosphate |
| DIAD | diisoproppyl azodicarboxylate |
| DIC | diisopropyl carbonyl diimide |
| DIEA | N,N-diisopropylethylamine |
| HATU | O-(7-azabenzotriazol-1-yl)-1,1,3,3-tetramethyluronium hexafluorophosphate |
| HOAt | 1-hydroxy-7-azabenzotriazole |
| HOBt | 1-hydroxybenzotriazole hydrate |
| MCPBA | 3-chloroperoxybenzoic acid |
| PyBOP | benzotriazol-1-yloxy-tris(pyrrolidino)phosphonium hexafluorophosphate |
| TFA | trifluoroacetic acid |
| TPP | triphenylphosphine |
| Solvents: | |
| DCM | dichloromethane |
| DMF | dimethylformamide |
| DMSO | dimethylsulfoxide |
| $Et_2O$ | diethyl ether |
| MeOH | methanol |
| THF | tetrahydrofuran |
| Protecting Groups: | |
| All | allyl |
| Alloc | allyloxy carbonyl |
| Fmoc | 9-fluorenylmethoxy carbonyl |
| tButyl | tertiary-Butyl |
| Trt | triphenylmethyl |
| Others: | |
| Dess-Martin | Dess-Martin periodinane |
| LC/MS | HPLC/Mass spectrometry |
| rt | room temperature |

The reactions were carried out in but not limited to the following: plastic disposable syringes of the appropriate size, each fitted with a polypropylene frit to retain the resin, 1-10 ml reaction vessel compatible with Symphony Automated Peptide Synthesizer (Protein Technologies), ACT 90 Synthesizer (Advanced ChemTech), Robbins block, or IRORI system.

LCMS analysis was performed on reverse-phase $C_{18}$ Zorbax columns using the following solvent system: A, water with 0.1% formic acid; B, acetonitrile with 0.1% formic acid.

The following conditions were applied: column 2.1×30 mm, 5-95% B in 3 min (for compounds of Tables 3 and 4) or 4 min (for compounds of Table 5), flow 0.8 ml/min. Mass spectra for separated peaks were obtained by electrospray (ES) using a MicroMass LCZ mass spectrometer.

EXAMPLES

These examples illustrate the synthesis of representative helix mimetics of this invention. The solid phase syntheses of these helix mimetics demonstrate that libraries containing such members may be readily prepared. Structures of representative helix mimetics are given in Table 3, 4 and 5.

Example 1

Solid Phase Synthesis of Representative Helix Mimetic

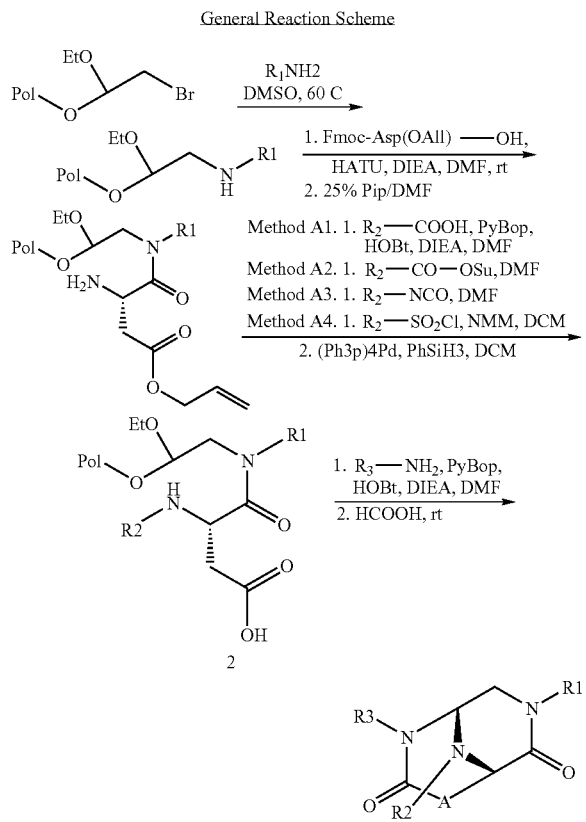

Commercially available 2-bromo-1-ethoxy-1-oxy-polystyrene resin (Pol-O—CH(OEt)—CH$_2$Br) (Advanced ChemTech) was suspended in DMSO to which an amine (10 equivalents) was added. The resulting mixture was mechanically stirred using an overhead stirrer and heated to 60° C. After 24 h, the resin was filtered and washed sequentially with DMSO, DMF, MeOH, DMF, MeOH, Et$_2$O then dried in vacuo. The substitution of the resin was determined spectroscopically by the Fmoc release method.

The secondary amine resin resin (Pol-O—CH(OEt)-CH$_2$NH—R$_1$) was contacted with a 0.05 N solution of α-N-Fmoc-γ-O-allyl-aspartic acid (Fmoc-Asp(OAll)OH), HATU and DIEA in DMF (4 equivalents). The resulting mixture was agitated for 2 h then tested against chloranil/acetaldehyde for complete reaction. Upon a negative chloranil test, the resin was filtered, sequentially washed with DMF, MeOH, DMF, MeOH. The Fmoc carbamate was deprotected by contacting the resin with 25% piperidine/DMF at room temperature. Following 1 h, the resin was drained, and washed sequentially with DMF, MeOH, DMF, MeOH, Et$_2$O and dried in vacuo.

Method A1

The deprotected resin (Pol-O—CH(OEt)-CH$_2$—N—(R$_1$)—CO—CH—(CH$_2$CO$_2$CH$_2$CH═CH$_2$)—NH$_2$) was contacted with a 0.04 N solution of the carboxylic acid (R2), PyBop, HOBt and DIEA in DMF (3 equivalents). The reaction was tested for completeness using the Kaiser ninhydrin test after 1 h. Once the reaction was found to be complete, the resin was drained, and sequentially washed with DMF, MeOH, DMF, MeOH and Et$_2$O then dried in vacuo.

Method A2

The deprotected resin (Pol-O—CH(OEt)-CH$_2$—N—(R$_1$)—CO—CH—(CH$_2$CO$_2$CH$_2$CH═CH$_2$)—NH$_2$) was contacted with a 0.04 N solution of a N-hydroxysuccinimyl carbonate (R2) in DMF (3 equivalents). After 2 h the reaction was checked for completeness using the Kaiser ninhydrin test. Once the reaction was found to be complete, the resin was drained and washed sequentially with DMF, MeOH, DMF, MeOH and Et$_2$O then dried in vacuo.

Method A3

The deprotected resin (Pol-O—CH(OEt)-CH$_2$—N—(R$_1$)—CO—CH—(CH$_2$CO$_2$CH$_2$CH═CH$_2$)—NH$_2$) was contacted with a 0.04 N solution of an isocyanate (R2) in DMF (3 equivalents). After 2 h the reaction was checked for completeness using the Kaiser ninhydrin test. Once the reaction was found to be complete, the resin was drained and washed sequentially with DMF, MeOH, DMF, MeOH and Et$_2$O then dried in vacuo.

Method A4

The deprotected resin (Pol-O—CH(OEt)-CH$_2$—N—(R$_1$)—CO—CH—(CH$_2$CO$_2$CH$_2$CH═CH$_2$)—NH$_2$) was contacted with a 0.05 N solution of sulphonyl chloride (R2) and N-methylmorpholine in DCM (4 equivalents). After 2 h the reaction was checked for completeness using the Kaiser ninhydrin test. Once the reaction was found to be complete, the resin was drained and washed sequentially with DCM, MeOH, DCM, MeOH and Et$_2$O then dried in vacuo.

Allyl Deprotection

The allyl ester resin resulting from Method A1-A4 was deprotected by contacting with a solution of 0.02 N (Ph$_3$P)$_4$ Pd$^0$, Ph$_3$P and 0.20 N PhSiH$_3$ in DCM for 2 h. The resin was then filtered and washed sequentially with DCM (2×), MeOH, DCM, MeOH and DCM then dried in vacuo.

The resin containing the γ-carboxylic acid (Pol-O—CH (OEt)-CH$_2$—N(R$_1$)—CO—CH—(CH$_2$CO$_2$H)—NH$_2$) was contacted with a 0.04 N solution containing an amine (R$_3$—NH$_2$), PyBop, HOBt, and DIEA in DMF (3 equivalents). After 4 h, the resin was drained and washed sequentially with DMF, MeOH, DMF, MeOH and Et$_2$O, then dried in vacuo.

The resin resulting from the above method (Pol-O—CH (OEt)-CH$_2$—N—(R$_1$)—CO—CH—(CH$_2$CONHR$_3$)—NHR$_2$) was swelled with DCM then contacted with glacial formic acid (approximately 2 mL/50 mg resin) for 14 h. The resulting solution was drained and the resin washed with 10% (v/v) formic acid/DCM (0.5 mL/50 mg resin). The combined solutions were evaporated in vacuo. The residue was dissolved in 50% (v/v) aqueous solution of acetonitrile, frozen to −76° C. and lyopholized.

Example 2

Synthesis of Representative Helix Mimetic

The representative compounds listed in Table 3 were synthesized according to the procedures set forth in Example 1.

TABLE 3

Representative Compounds of Structure Type (II″)

| Cpd | R1 | R2 | R3 | Method | LC RT | M + H+ |
|---|---|---|---|---|---|---|
| 1 | isopentyl-X1 | X2-CH2-C(O)-CH2-3,5-bis(trifluoromethyl)phenyl | 4-(2-X3-ethyl)morpholine | A1 | 1.57 | 607.3 |
| 2 | HO-C(O)-CH2CH2-X1 | isopropyl-NH-C(O)-X2 | cyclohexyl-X3 | A3 | 1.34 | 395.2 |
| 3 | (CH3)2N-(CH2)6-X1 | X2-SO2-(5-chloro-1,3-dimethylpyrazol-4-yl) | 1-(3-X3-propyl)imidazole | A4 | 0.75 | 583.3 |
| 4 | HO-C(O)-CH2CH2-X1 | X2-CH2-C(O)-CH2-3,5-bis(trifluoromethyl)phenyl | cyclohexyl-X3 | A1 | 1.78 | 578.2 |
| 5 | (CH3)2N-(CH2)6-X1 | X2-C(O)-NH-CH2CH2-phenyl | cyclohexyl-X3 | A3 | 1.33 | 512.4 |

TABLE 3-continued
Representative Compounds of Structure Type (II″)
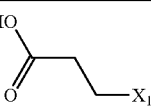
(II″)
| Cpd | R1 | R2 | R3 | Method | LC RT | M + H⁺ |
|---|---|---|---|---|---|---|
| 6 | 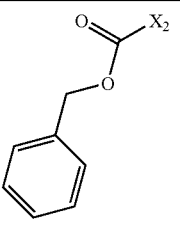 | 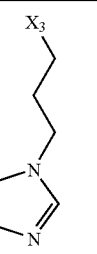 | 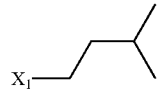 | A2 | 0.97 | 470.2 |
| 7 | 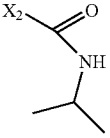 | 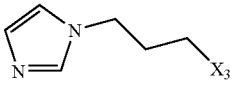 | 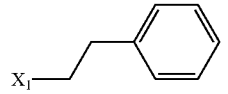 | A3 | 1.04 | 419.3 |
| 8 |  | 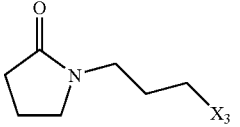 | 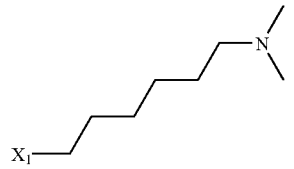 | A3 | 1.45 | 532.3 |
| 9 | 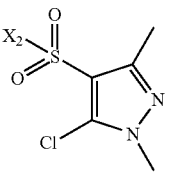 | 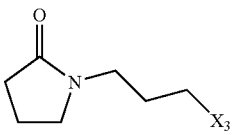 | 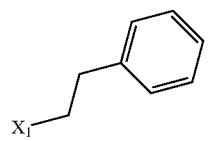 | A4 | 0.97 | 600.3 |
| 10 | 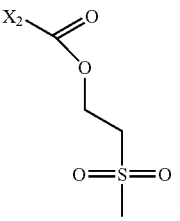 | 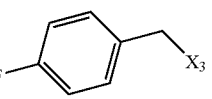 | 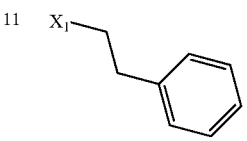 | A2 | 1.49 | 518.2 |
| 11 | 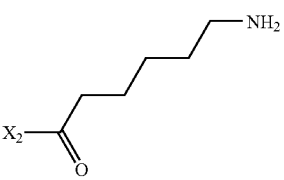 | 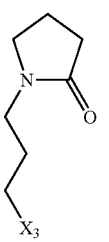 | | A1 | 1.06 | 498.3 |

TABLE 3-continued

Representative Compounds of Structure Type (II")

(II")

| Cpd | R1 | R2 | R3 | Method | LC RT | M + H⁺ |
|---|---|---|---|---|---|---|
| 12 | HO-C(O)-CH₂CH₂-X₁ | 5-chloro-1,3-dimethyl-1H-pyrazol-4-yl sulfonyl-X₂ | morpholin-4-yl-ethyl-X₃ | A4 | 0.84 | 533.2 |
| 13 | phenethyl-X₁ | isopropyl-NH-C(O)-X₂ | 2-oxopyrrolidin-1-yl-propyl-X₃ | A3 | 1.36 | 470.3 |
| 14 | HO-C(O)-CH₂CH₂-X₁ | phenethyl-NH-C(O)-X₂ | imidazol-1-yl-propyl-X₃ | A3 | 1.01 | 483.2 |
| 15 | phenethyl-X₁ | phenylsulfonyl-X₂ | cyclohexyl-X₃ | A4 | 1.8 | 482.2 |
| 16 | phenethyl-X₁ | 3,5-bis(trifluoromethyl)phenyl-propanoyl-X₂ | 2-oxopyrrolidin-1-yl-propyl-X₃ | A1 | 1.96 | 653.3 |
| 17 | HO-C(O)-CH₂CH₂-X₁ | 2-(methylsulfonyl)ethoxy-C(O)-X₂ | 2-oxopyrrolidin-1-yl-propyl-X₃ | A2 | 0.84 | 503.2 |

TABLE 3-continued

Representative Compounds of Structure Type (II")

(II")

| Cpd | R1 | R2 | R3 | Method | LC RT | M + H⁺ |
| --- | --- | --- | --- | --- | --- | --- |
| 18 | X₁-(CH₂)₆-N(CH₃)₂ | X₂-C(O)-NH-CH₂CH₂-Ph | morpholine-N-CH₂CH₂-X₃ | A3 | 0.87 | 543.4 |
| 19 | X₁-CH₂CH₂CH(CH₃)₂ | X₂-C(O)-NH-CH₂CH₂-Ph | 2-oxopyrrolidin-1-yl-(CH₂)₃-X₃ | A3 | 1.5 | 498.3 |
| 20 | X₁-CH₂CH₂-Ph | X₂-C(O)-(CH₂)₅-NH₂ | morpholine-N-CH₂CH₂-X₃ | A1 | 0.74 | 486.3 |
| 21 | X₁-CH₂CH₂CH(CH₃)₂ | X₂-SO₂-(5-chloro-1,3-dimethylpyrazol-4-yl) | cyclohexyl-X₃ | A4 | 1.65 | 500.2 |
| 22 | Ph-CH₂CH₂-X₁ | iPr-NH-C(O)-X₂ | 1H-indol-3-yl-CH₂CH₂-X₃ | A3 | 1.57 | 488.3 |

TABLE 3-continued

Representative Compounds of Structure Type (II″)

(II″)

| Cpd | R1 | R2 | R3 | Method | LC RT | M + H+ |
|---|---|---|---|---|---|---|
| 23 | isopentyl-X1 | X2-C(O)-(CH2)5-NH2 | indol-3-yl-ethyl-X3 | A1 | 1.36 | 482.3 |
| 24 | phenethyl-X1 | methylsulfonyl-ethyl-O-C(O)-X2 | indol-3-yl-ethyl-X3 | A2 | 0.97 | 553.2 |
| 25 | HOOC-CH2CH2-X1 | X2-C(O)-(CH2)5-NH2 | indol-3-yl-ethyl-X3 | A1 | 0.27 | 484.3 |
| 26 | phenethyl-X1 | 3,5-bis(trifluoromethyl)phenyl-CH2CH2-C(O)-X2 | 4-fluorobenzyl-X3 | A1 | 2.02 | 636.5 |
| 27 | Me2N-(CH2)5-X1 | 3,5-bis(trifluoromethyl)phenyl-CH2CH2-C(O)-X2 | 4-fluorobenzyl-X3 | A1 | 1.47 | 658.3 |

TABLE 3-continued

Representative Compounds of Structure Type (II'')

(II'')

| Cpd | R1 | R2 | R3 | Method | LC RT | M + H⁺ |
|---|---|---|---|---|---|---|
| 28 | isopentyl-X₁ | phenylsulfonyl-X₂ | morpholinoethyl-X₃ | A4 | 1.15 | 479.5 |
| 29 | isopentyl-X₁ | methylsulfonylethoxycarbonyl-X₂ | 4-fluorobenzyl-X₃ | A2 | 1.49 | 484.5 |
| 30 | isopentyl-X₁ | 3-(3,5-bis(trifluoromethyl)phenyl)propanoyl-X₃ | 4-fluorobenzyl-X₃ | A1 | 2.05 | 602.5 |

Example 3

Synthesis of Representative Helix Mimetic

General Reaction Scheme

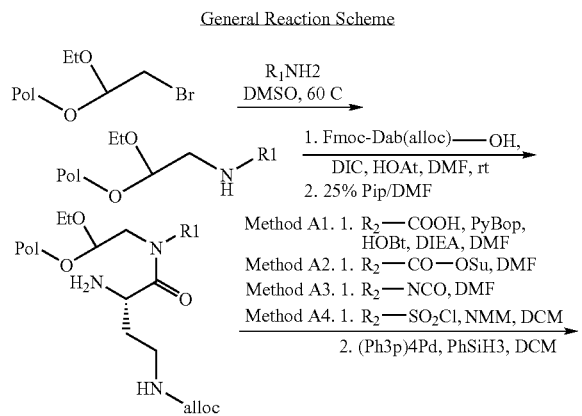

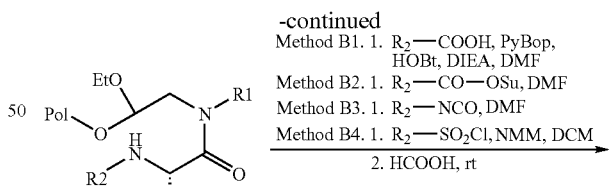

-continued

Method B1. 1. R₂—COOH, PyBop, HOBt, DIEA, DMF
Method B2. 1. R₂—CO—OSu, DMF
Method B3. 1. R₂—NCO, DMF
Method B4. 1. R₂—SO₂Cl, NMM, DCM
2. HCOOH, rt

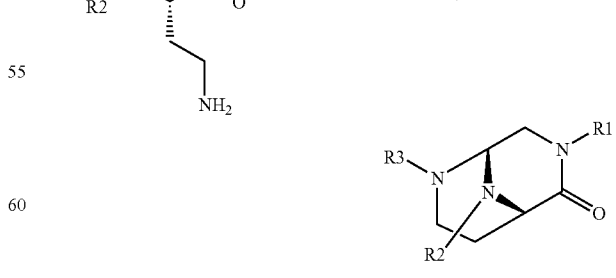

Commercially available 2-bromo-1-ethoxy-1-oxy-polystyrene resin (Pol-O—CH(OEt)—CH₂—Br) (Advanced ChemTech) was suspended in DMSO to which an amine, R₁NH₂, (10 equivalents) was added. The resulting mixture was mechanically stirred using an overhead stirrer and heated to 60° C. After 24 h, the resin was filtered and washed sequentially with DMSO, DMF, MeOH, DMF, MeOH, and $Et_2O$ then dried in vacuo. The substitution of the resin was determined spectroscopically by the Fmoc release method.

The secondary amine resin (Pol-O—CH(OEt)-$CH_2$—$NHR_1$) was contacted with a 0.05 N solution of α-Fmoc-β-Alloc-2,4-diamanobutyric acid (Fmoc-Dab(Alloc)OH), HATU and DIEA in DMF (4 equivalents). The resulting mixture was agitated for 2 h then tested against chloranil/acetaldehyde for complete reaction. Upon a negative chloranil test, the resin was filtered, sequentially washed with DMF, MeOH, DMF and MeOH. The Fmoc was deprotected by contacting the resin with 25% piperidine/DMF at room temperature. Following 1 h, the resin was drained, and washed sequentially with DMF, MeOH, DMF, MeOH and $Et_2O$ and dried in vacuo.

Method A1

The deprotected Alloc-resin (Pol-O—CH(OEt)-$CH_2$—$NR_1$—C(=O)—CH($CH_2CH_2$NH-Alloc)-$NH_2$) was contacted with carboxylic acid ($R_2CO_2H$) and treated as previously described.

Method A2

The deprotected Alloc-resin (Pol-O—CH(OEt)-$CH_2$—$NR_1$—C(=O)—CH($CH_2CH_2$NH-Alloc)-$NH_2$) was contacted with N-hydroxysuccinimyl carbonate ($R_2CO_2$Su) and treated as previously described.

Method A3

The deprotected Alloc-resin (Pol-O—CH(OEt)-$CH_2$—$NR_1$—C(=O)—CH($CH_2CH_2$NH-Alloc)-$NH_2$) was contacted with an isocyanate ($R_2$NCO) and treated as previously described.

Method A4

The deprotected Alloc-resin (Pol-O—CH(OEt)-$CH_2$—$NR_1$—C(=O)—CH($CH_2CH_2$NH-Alloc)-$NH_2$) was contacted with a solution of sulphonyl chloride ($R_2SO_2$Cl) and treated as previously described.

Alloc Deprotection

The Alloc carbamate resin resulting from Method A1-A4 was deprotected by contacting with a solution of 0.02 N $(Ph_3P)_4Pd^0$, $Ph_3P$ and 0.20 N $PhSiH_3$ in DCM for 2 h. The resin was then filtered and washed sequentially with DCM (2×), MeOH, DCM, MeOH and DCM then dried in vacuo.

Method B1

The Alloc deprotected resin (Pol-O—CH(OEt)-$CH_2$—$NR_1$—C(=O)—CH($CH_2CH_2NH_2$)—$NH_2$) was contacted with a 0.04 N solution of the carboxylic acid ($R_3CO_2H$), PyBop, HOBt and DIEA in DMF (3 equivalents). The reaction was tested for completeness using the Kaiser ninhydrin test after 1 h. Once the reaction was found to be complete, the resin was drained, and sequentially washed with DMF, MeOH, DMF, MeOH and $Et_2O$ then dried in vacuo.

Method B2

The Alloc deprotected resin (Pol-O—CH(OEt)-$CH_2$—$NR_1$—C(=O)—CH($CH_2CH_2NH_2$)—$NH_2$) was contacted with a 0.04 N solution of a N-hydroxysuccinimyl carbonate ($R_3CO_2$Su) in DMF (3 equivalents). After 2 h the reaction was checked for completeness using the Kaiser ninhydrin test. Once the reaction was found to be complete, the resin was drained and washed sequentially with DMF, MeOH, DMF, MeOH and $Et_2O$ then dried in vacuo.

Method B3

The Alloc deprotected resin (Pol-O—CH(OEt)-$CH_2$—$NR_1$—C(=O)—CH($CH_2CH_2NH_2$)—$NH_2$) was contacted with a 0.04 N solution of an isocyanate ($R_3$NCO) in DMF (3 equivalents). After 2 h the reaction was checked for completeness using the Kaiser ninhydrin test. Once the reaction was found to be complete, the resin was drained and washed sequentially with DMF, MeOH, DMF, MeOH and $Et_2O$ then dried in vacuo.

Method B4

The Alloc deprotected resin (Pol-O—CH(OEt)-$CH_2$—$NR_1$—C(=O)—CH($CH_2CH_2NH_2$)—$NH_2$) was contacted with a 0.05 N solution of sulphonyl chloride ($R_3SO_2$Cl) and N-methylmorpholine in DCM (4 equivalents). After 2 h the reaction was checked for completeness using the Kaiser ninhydrin test. Once the reaction was found to be complete, the resin was drained and washed sequentially with DCM, MeOH, DCM, MeOH and $Et_2O$ then dried in vacuo.

The resin resulting from Methods B1-B4 was swelled with DCM then contacted with glacial formic acid (approximately 2 mL/50 mg resin) for 14 h. The resulting solution was drained and the resin washed with 10% (v/v) formic acid/DCM (0.5 mL/50 mg resin). The combined solutions were evaporated in vacuo. The residue was dissolved in 50% (v/v) aqueous solution of acetonitrile, frozen to −76° C. and lyopholized.

Example 4

Synthesis of Representative Helix Mimetic

The representative compounds listed in Table 4 were synthesized according to the procedures set forth in Example 3.

TABLE 4
Representative Compounds of Structure Type (III″)
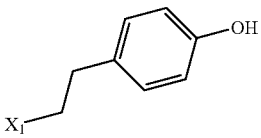
(III″)
| Cpd | R1 | R2 | R3 | Method | LC RT | M + H+ |
|---|---|---|---|---|---|---|
| 31 | 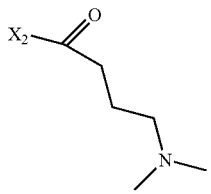 | 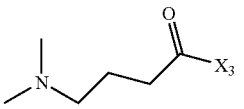 | 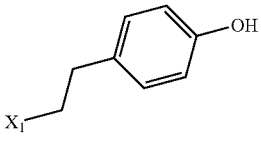 | A1, B1 | 0.59 | 488.5 |
| 32 | 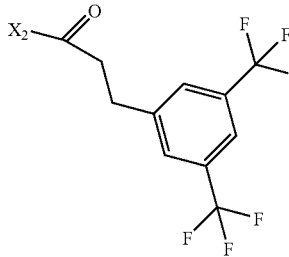 | 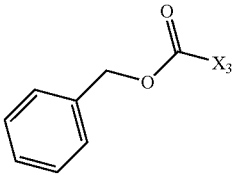 | 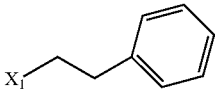 | A1, B2 | 1.82 | 664.4 |
| 33 | 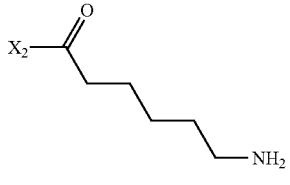 | 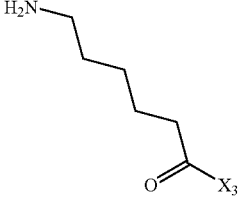 | 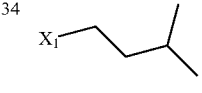 | A1, B1 | 0.76 | 472.5 |
| 34 | 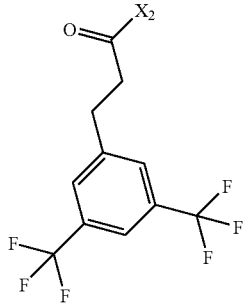 | 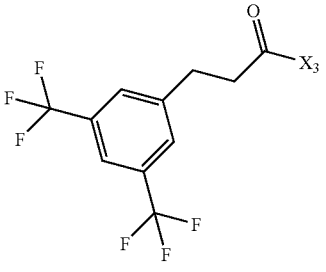 | 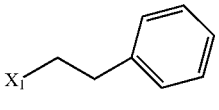 | A1, B1 | 2.2 | 748.4 |
| 35 | 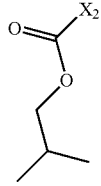 | 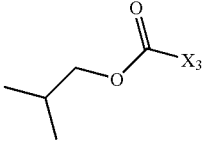 | | A2, B2 | 2.82 | 446.5 |

TABLE 4-continued

Representative Compounds of Structure Type (III″)

(III″)

| Cpd | R1 | R2 | R3 | Method | LC RT | M+H+ |
|---|---|---|---|---|---|---|
| 36 | methoxypropyl-X1 | X2-C(O)-(CH2)5-NH2 | benzyl-NH-C(O)-X3 | A1, B3 | 0.89 | 460.5 |
| 37 | phenethyl-X1 | benzyl-NH-C(O)-X2 | 3,5-bis(trifluoromethyl)phenyl-CH2CH2-C(O)-X3 | A3, B1 | 1.85 | 647.4 |
| 38 | phenethyl-X1 | isobutyl-O-C(O)-X2 | ethyl-O-C(O)-X3 | A2, B2 | 1.64 | 418.4 |
| 39 | 3,4-dimethoxyphenethyl-X1 | benzyl-O-C(O)-X2 | benzyl-O-C(O)-X3 | A2, B2 | 1.71 | 574.5 |
| 40 | isopentyl-X1 | isobutyl-O-C(O)-X2 | benzyl-O-C(O)-X3 | A2, B2 | 1.86 | 446.5 |
| 41 | (CH3)2N-(CH2)6-X1 | (CH3)2N-(CH2)2-C(O)-X2 | ethyl-O-C(O)-X3 | A1, B2 | 0.63 | 454.5 |

TABLE 4-continued
Representative Compounds of Structure Type (III″)
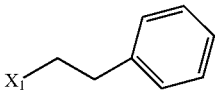
(III″)
| Cpd | R1 | R2 | R3 | Method | LC RT | M + H+ |
|---|---|---|---|---|---|---|
| 42 | 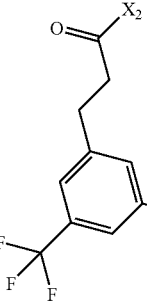 | 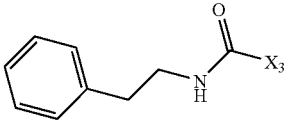 | 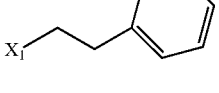 | A1, B3 | 1.89 | 661.5 |
| 43 | 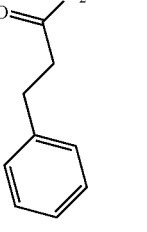 | 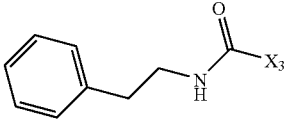 | 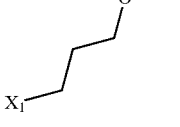 | A1, B3 | 1.84 | 478.5 |
| 44 | 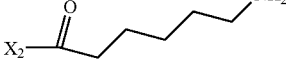 | 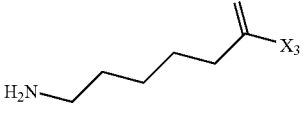 | 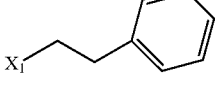 | A1, B1 | 0.41 | 440.5 |
| 45 | 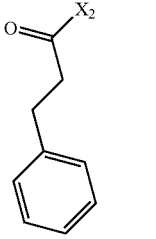 | 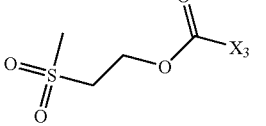 | 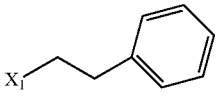 | A1, B2 | 1.37 | 528.4 |
| 46 | 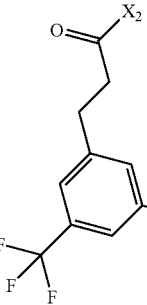 | 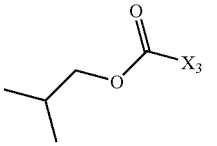 | | A1, B2 | 2.02 | 614.4 |

TABLE 4-continued

Representative Compounds of Structure Type (III")

(III")

| Cpd | R1 | R2 | R3 | Method | LC RT | M + H+ |
|---|---|---|---|---|---|---|
| 47 | phenethyl | 2-(methylsulfonyl)ethyl carbonate | ethyl carbamate | A2, B1 | 1.74 | 468.4 |
| 48 | phenethyl | 3-[3,5-bis(trifluoromethyl)phenyl]propanoyl | 5-chloro-1,3-dimethyl-1H-pyrazole-4-sulfonyl | A1, B4 | 1.87 | 706.4 |
| 49 | 2-(3,4-dimethoxyphenyl)ethyl | isobutyl carbonate | 3-[3,5-bis(trifluoromethyl)phenyl]propanoyl | A2, B1 | 0.11 | 674.5 |
| 50 | 2-(4-hydroxyphenyl)ethyl | 3-phenylpropanoyl | benzylcarbamoyl | A1, B3 | 1.4 | 527.5 |
| 51 | 2-(3,4-dimethoxyphenyl)ethyl | 3-phenylpropanoyl | 3-[3,5-bis(trifluoromethyl)phenyl]propanoyl | A1, B1 | 0.04 | 706.5 |

TABLE 4-continued
Representative Compounds of Structure Type (III″)
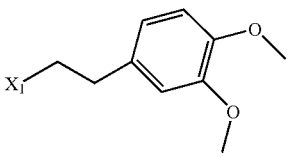
(III″)
| Cpd | R1 | R2 | R3 | Method | LC RT | M + H+ |
|---|---|---|---|---|---|---|
| 52 | 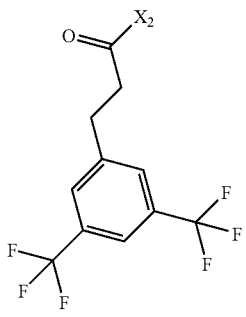 | 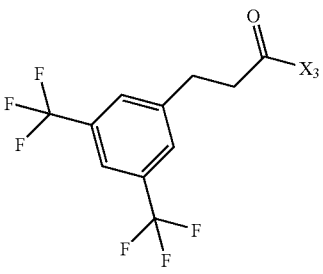 | 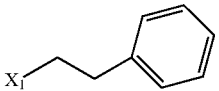 | A1, B1 | 2.2 | 782.4 |
| 53 | 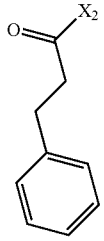 | 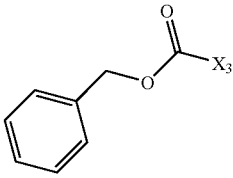 | 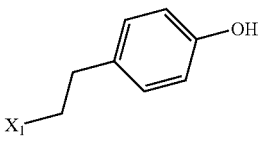 | A1, B2 | 1.76 | 512.5 |
| 54 | 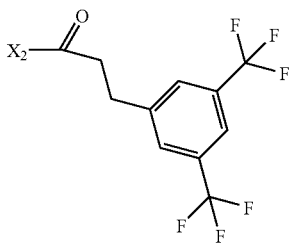 | 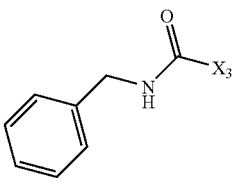 | 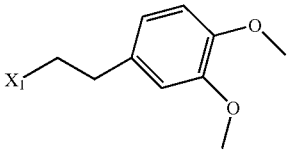 | A1, B3 | 1.71 | 663.4 |
| 55 | 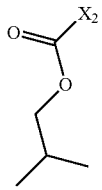 | 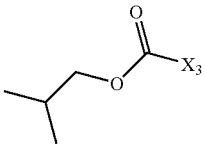 | 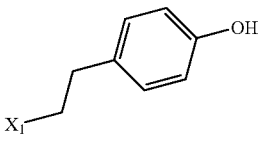 | A2, B2 | 1.68 | 506.5 |
| 56 | 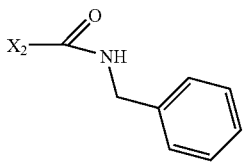 | 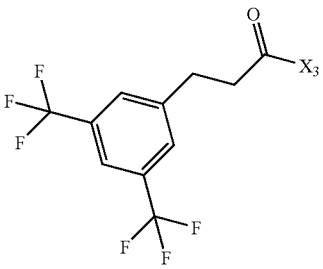 | | A3, B1 | 1.71 | 663.4 |

TABLE 4-continued
Representative Compounds of Structure Type (III″)
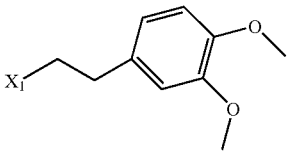
(III″)
| Cpd | R1 | R2 | R3 | Method | LC RT | M+H+ |
|---|---|---|---|---|---|---|
| 57 | 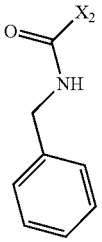 | 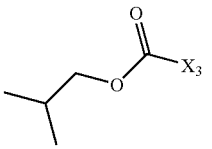 | 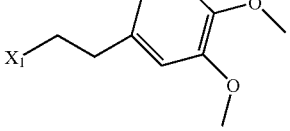 | A3, B2 | 1.53 | 539.5 |
| 58 | 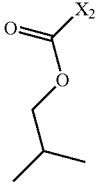 | 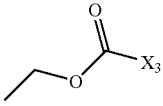 | 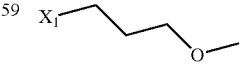 | A2, B2 | 1.51 | 478.5 |
| 59 | 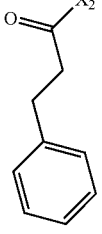 | 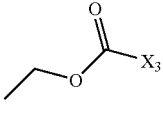 | 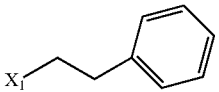 | A1, B2 | 1.31 | 418.4 |
| 60 | 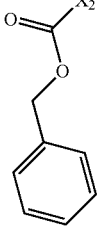 | 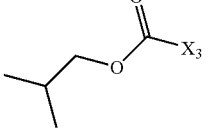 | 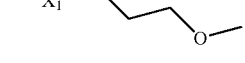 | A2, B2 | 1.82 | 480.4 |
| 61 | 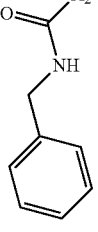 | 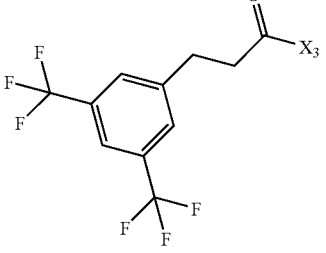 | | A3, B1 | 1.69 | 615.4 |

TABLE 4-continued

Representative Compounds of Structure Type (III")

(III")

| Cpd | R1 | R2 | R3 | Method | LC RT | M + H+ |
|---|---|---|---|---|---|---|
| 62 | 4-hydroxyphenethyl | benzyl carbonate | 3-(3,5-bis(trifluoromethyl)phenyl)propanoyl | A2, B1 | 1.81 | 664.4 |
| 63 | isopentyl | 3-(3,5-bis(trifluoromethyl)phenyl)propanoyl | 4-nitrobenzyl carbonate | A1, B2 | 1.97 | 659.4 |
| 64 | phenethyl | 3-(3,5-bis(trifluoromethyl)phenyl)propanoyl | benzyl carbonate | A1, B2 | 1.99 | 648.4 |
| 65 | 6-(dimethylamino)hexyl | benzyl carbonate | 4-(dimethylamino)butanoyl | A2, B1 | 0.82 | 516.6 |

TABLE 4-continued

Representative Compounds of Structure Type (III")

| Cpd | R1 | R2 | R3 | Method | LC RT | M+H+ |
|---|---|---|---|---|---|---|
| 66 | 4-hydroxyphenethyl | 5-aminopentanoyl | benzyloxycarbonyl | A1, B2 | 1 | 509.5 |
| 67 | 4-hydroxyphenethyl | 4-(dimethylamino)butanoyl | 3-(3,5-bis(trifluoromethyl)phenyl)propanoyl | A1, B1 | 2.1 | 643.5 |
| 68 | 3,4-dimethoxyphenethyl | benzyloxycarbonyl | 4-nitrobenzyloxycarbonyl | A2, B2 | 1.71 | 619.4 |
| 69 | isopentyl | 2-(methylsulfonyl)ethoxycarbonyl | phenethylaminocarbonyl | A2, B3 | 1.36 | 509.4 |
| 70 | phenethyl | benzylaminocarbonyl | isobutyloxycarbonyl | A3, B2 | 1.64 | 479.5 |

TABLE 4-continued
Representative Compounds of Structure Type (III")
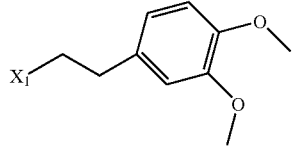
(III")
| Cpd | R1 | R2 | R3 | Method | LC RT | M+H+ |
|---|---|---|---|---|---|---|
| 71 | 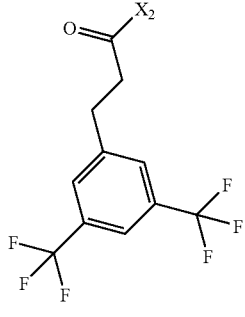 | 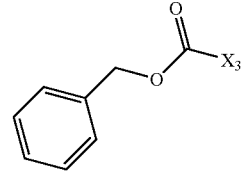 | 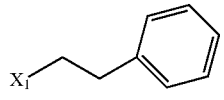 | A1, B2 | 1.91 | 708.4 |
| 72 | 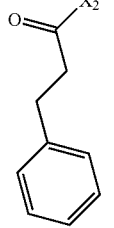 | 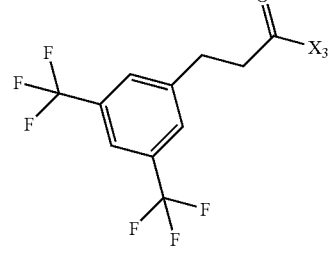 | 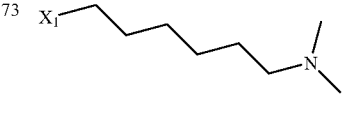 | A1, B1 | 1.94 | 646.4 |
| 73 | 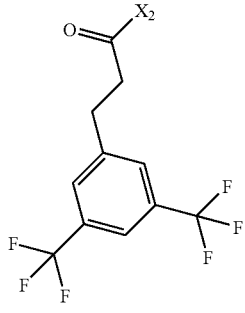 | 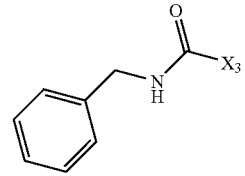 | 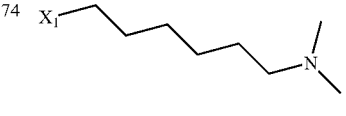 | A1, B3 | 1.38 | 670.5 |
| 74 | 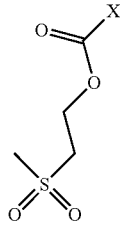 | 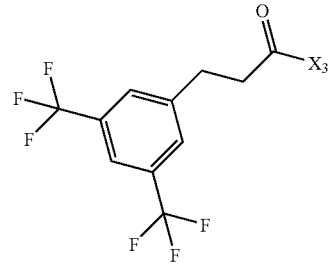 | | A2, B1 | 1.58 | 687.5 |

TABLE 4-continued

Representative Compounds of Structure Type (III")

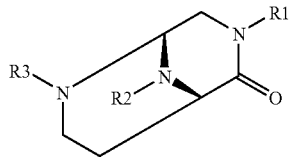

(III")

| Cpd | R1 | R2 | R3 | Method | LC RT | M + H+ |
|---|---|---|---|---|---|---|
| 75 | X1-CH2CH2-phenyl | X2-C(O)-CH2CH2-[3,5-bis(trifluoromethyl)phenyl] | X3-C(O)O-CH2-(4-nitrophenyl) | A1, B2 | 1.99 | 693.4 |
| 76 | X1-CH2CH2CH2-OCH3 | X2-C(O)-CH2CH2-[3,5-bis(trifluoromethyl)phenyl] | X3-C(O)O-CH2-phenyl | A1, B2 | 1.86 | 616.4 |
| 77 | X1-CH2CH2CH2-OCH3 | X2-C(O)-CH2CH2-[3,5-bis(trifluoromethyl)phenyl] | X3-C(O)O-CH2-(4-nitrophenyl) | A1, B2 | 1.79 | 661.4 |
| 78 | X1-CH2CH2CH2-OCH3 | X2-C(O)-CH2CH2-[3,5-bis(trifluoromethyl)phenyl] | X3-C(O)NH-CH2-phenyl | A1, B3 | 1.72 | 615.4 |

TABLE 4-continued
Representative Compounds of Structure Type (III'')
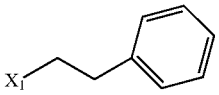
(III'')
| Cpd | R1 | R2 | R3 | Method | LC RT | M+H+ |
|---|---|---|---|---|---|---|
| 79 | 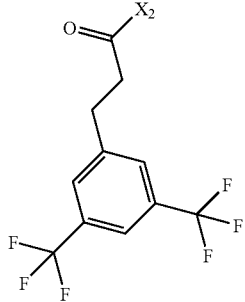 | 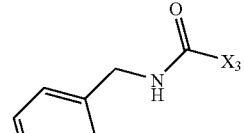 | 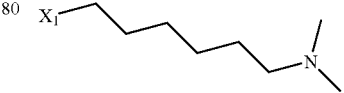 | A1, B3 | 1.86 | 647.4 |
| 80 | 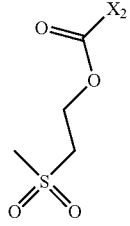 | 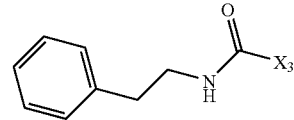 | 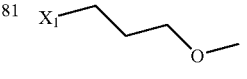 | A2, B3 | 0.93 | 566.5 |
| 81 | 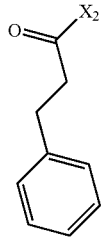 | 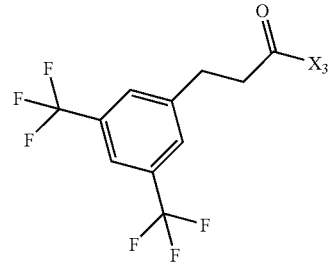 | 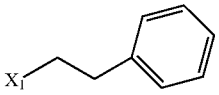 | A1 B1 | 1.79 | 614.4 |
| 82 | 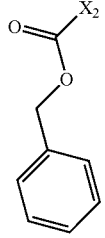 | 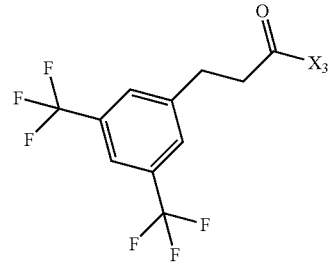 |  | A2, B1 | 1.99 | 648.4 |

TABLE 4-continued

Representative Compounds of Structure Type (III'')

(III'')

| Cpd | R1 | R2 | R3 | Method | LC RT | M+H+ |
|---|---|---|---|---|---|---|
| 83 | isobutyl | 3-(3,5-bis(trifluoromethyl)phenyl)propanoyl | benzyloxycarbonyl | A1, B2 | 2.04 | 614.4 |
| 84 | 3-methoxypropyl | 4-(dimethylamino)butanoyl | 3-(3,5-bis(trifluoromethyl)phenyl)propanoyl | A1, B1 | 1.21 | 595.5 |
| 85 | isobutyl | benzyloxycarbonyl | benzyloxycarbonyl | A2, B2 | 1.85 | 480.4 |
| 86 | 6-(dimethylamino)hexyl | 4-(dimethylamino)butanoyl | 4-nitrobenzyloxycarbonyl | A1, B2 | 1.48 | 542.2 |
| 87 | 2-phenylethyl | 2-(methylsulfonyl)ethoxycarbonyl | 3-phenylpropanoyl | A2, B1 | 1.42 | 528.4 |

TABLE 4-continued
Representative Compounds of Structure Type (III'')
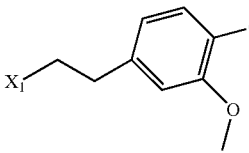
(III'')
| Cpd | R1 | R2 | R3 | Method | LC RT | M+H+ |
|---|---|---|---|---|---|---|
| 88 | 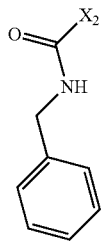 | 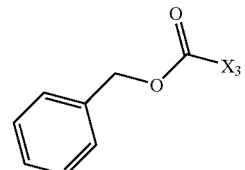 | 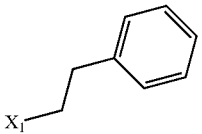 | A3, B2 | 1.56 | 573.5 |
| 89 | 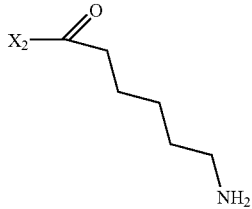 | 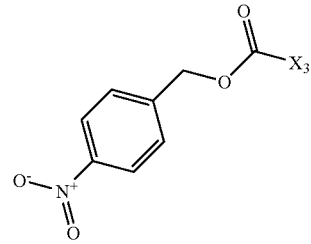 | 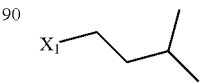 | A1, B2 | 1.14 | 538.5 |
| 90 | 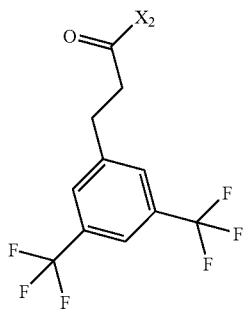 | 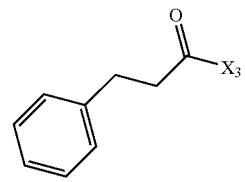 | 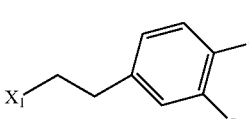 | A1, B1 | 1.98 | 612.5 |
| 91 | 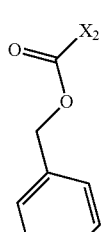 | 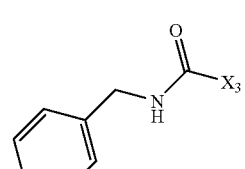 |  | A2, B3 | 1.66 | 587.5 |

TABLE 4-continued

Representative Compounds of Structure Type (III'')

(III'')

| Cpd | R1 | R2 | R3 | Method | LC RT | M+H+ |
|-----|----|----|----|--------|-------|------|
| 92 | 3,4-dimethoxyphenethyl-X1 | 3-(3,5-bis(trifluoromethyl)phenyl)propanoyl-X2 | benzylaminocarbonyl-X3 | A1, B3 | 1.68 | 707.5 |
| 93 | 3,4-dimethoxyphenethyl-X1 | 3-(3,5-bis(trifluoromethyl)phenyl)propanoyl-X2 | isobutoxycarbonyl-X3 | A1, B2 | 1.84 | 674.5 |
| 94 | 3,4-dimethoxyphenethyl-X1 | 3-phenylpropanoyl-X2 | benzylaminocarbonyl-X3 | A1, B3 | 1.52 | 571.5 |
| 95 | 3,4-dimethoxyphenethyl-X1 | 2-(methylsulfonyl)ethoxycarbonyl-X2 | ethoxycarbonyl-X3 | A2, B2 | 1.25 | 528.4 |

TABLE 4-continued
Representative Compounds of Structure Type (III″)
(III″)
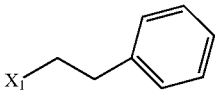
| Cpd | R1 | R2 | R3 | Method | LC RT | M+H+ |
|---|---|---|---|---|---|---|
| 96 | 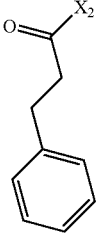 | 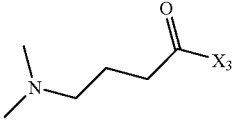 | 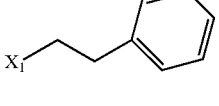 | A1, B1 | 1.18 | 491.5 |
| 97 | 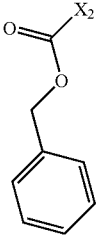 | 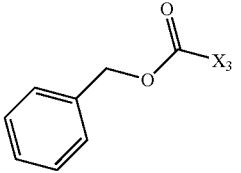 | 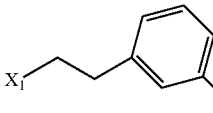 | A2, B2 | 1.82 | 514.4 |
| 98 | 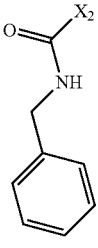 | 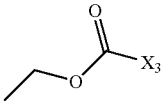 | 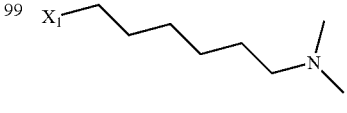 | A3, B2 | 1.36 | 511.5 |
| 99 | 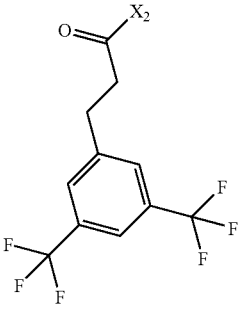 | 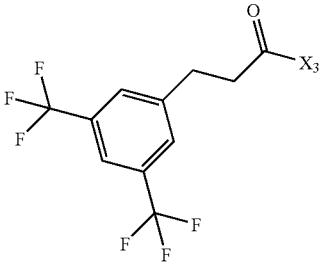 | | A1, B1 | 1.61 | 805.5 |

TABLE 4-continued

Representative Compounds of Structure Type (III'')

(III'')

| Cpd | R1 | R2 | R3 | Method | LC RT | M+H+ |
|---|---|---|---|---|---|---|
| 100 | 4-hydroxyphenethyl | 3-phenylpropanoyl | 3-(3,5-bis(trifluoromethyl)phenyl)propanoyl | A1, B1 | 1.8 | 662.4 |
| 101 | 3-methoxypropyl | benzyloxycarbonyl | 4-nitrobenzyloxycarbonyl | A2, B2 | 1.6 | 527.4 |
| 102 | 3-methoxypropyl | benzyloxycarbonyl | 3-(3,5-bis(trifluoromethyl)phenyl)propanoyl | A2, B1 | 1.82 | 616.4 |
| 103 | isopentyl | benzylaminocarbonyl | 3-(3,5-bis(trifluoromethyl)phenyl)propanoyl | A3, B1 | 1.89 | 613.5 |

TABLE 4-continued

Representative Compounds of Structure Type (III″)

(III″)

| Cpd | R1 | R2 | R3 | Method | LC RT | M+H+ |
|-----|----|----|----|--------|-------|------|
| 104 | X1-(CH2)6-N(CH3)2 | 3-(3,5-bis(trifluoromethyl)phenyl)propanoyl-X2 | benzyloxycarbonyl-X3 | A1, B2 | 1.57 | 671.5 |
| 105 | X1-(CH2)3-OCH3 | 6-aminohexanoyl-X2 | 3-(3,5-bis(trifluoromethyl)phenyl)propanoyl-X3 | A1, B1 | 1.2 | 595.5 |
| 106 | X1-(CH2)3-OCH3 | isobutyloxycarbonyl-X2 | 3-(3,5-bis(trifluoromethyl)phenyl)propanoyl-X3 | A2, B1 | 1.82 | 582.4 |
| 107 | X1-CH2CH2-(3,4-dimethoxyphenyl) | 2-(methylsulfonyl)ethoxycarbonyl-X2 | isobutyloxycarbonyl-X3 | A2, B2 | 1.32 | 556.4 |

TABLE 4-continued
Representative Compounds of Structure Type (III″)
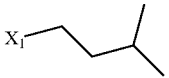
(III″)
| Cpd | R1 | R2 | R3 | Method | LC RT | M+H+ |
|---|---|---|---|---|---|---|
| 108 | 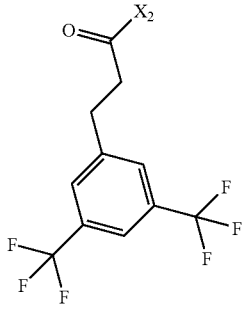 | 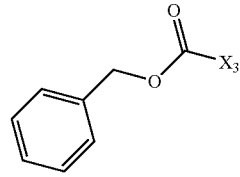 | 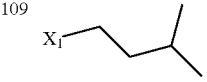 | A1, B3 | 1.89 | 613.5 |
| 109 | 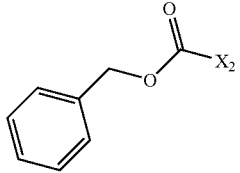 | 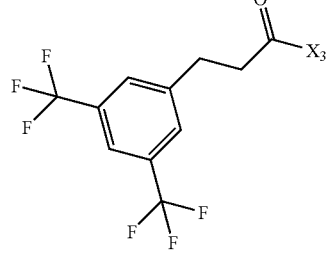 | 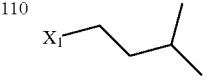 | A1, B1 | 2.02 | 614.4 |
| 110 | 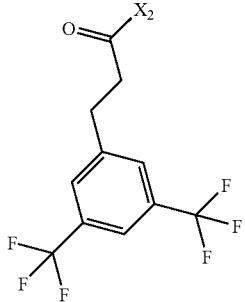 | 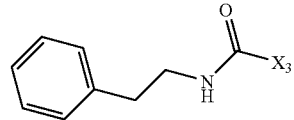 | 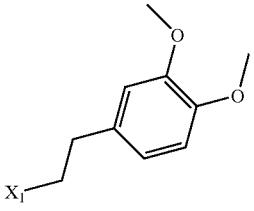 | A1, B3 | 1.93 | 627.5 |
| 111 | 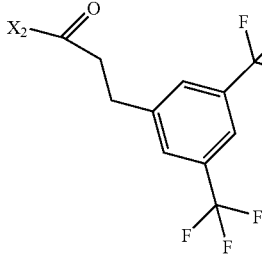 | 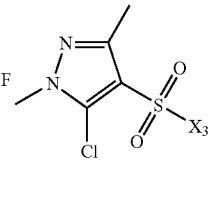 | | A1, B4 | 1.81 | 766.4 |

TABLE 4-continued

Representative Compounds of Structure Type (III")

(III")

| Cpd | R1 | R2 | R3 | Method | LC RT | M + H⁺ |
|-----|----|----|----|--------|-------|--------|
| 112 | phenethyl | N-benzyl carbamoyl | ethoxycarbonyl | A3, B2 | 1.48 | 451.4 |
| 113 | 6-(dimethylamino)hexyl | 3-phenylpropanoyl | 5-chloro-1,3-dimethyl-1H-pyrazole-4-sulfonyl | A1, B4 | 1.16 | 593.5 |
| 114 | 3,4-dimethoxyphenethyl | 3-(3,5-bis(trifluoromethyl)phenyl)propanoyl | 4-nitrobenzyloxycarbonyl | A1, B2 | 1.87 | 753.4 |
| 115 | 6-(dimethylamino)hexyl | 3-phenylpropanoyl | 3-(3,5-bis(trifluoromethyl)phenyl)propanoyl | A1, B1 | 1.93 | 669.5 |
| 116 | 6-(dimethylamino)hexyl | 3-(3,5-bis(trifluoromethyl)phenyl)propanoyl | 5-chloro-1,3-dimethyl-1H-pyrazole-4-sulfonyl | A1, B4 | 1.32 | 729.4 |

TABLE 4-continued

Representative Compounds of Structure Type (III'')

(III'')

| Cpd | R1 | R2 | R3 | Method | LC RT | M+H+ |
|-----|----|----|----|--------|-------|------|
| 117 | X1-(CH2)6-N(CH3)2 | isobutyl carbonate-X2 | benzyl carbonate-X3 | A2, B2 | 1.34 | 503.5 |
| 118 | X1-CH2CH2-(4-hydroxyphenyl) | 3,5-bis(trifluoromethyl)phenylpropanoyl-X2 | 4-nitrobenzyl carbonate-X3 | A1, B2 | 1.79 | 709.4 |
| 119 | X1-(CH2)3-OCH3 | 3,5-bis(trifluoromethyl)phenylpropanoyl-X2 | phenethyl carbamoyl-X3 | A1, B3 | 1.73 | 629.5 |
| 120 | X1-CH2CH2-(3,4-dimethoxyphenyl) | 3,5-bis(trifluoromethyl)phenylpropanoyl-X2 | phenethyl carbamoyl-X3 | A1, B3 | 1.81 | 721.5 |

TABLE 4-continued

Representative Compounds of Structure Type (III")

(III")

| Cpd | R1 | R2 | R3 | Method | LC RT | M + H+ |
|---|---|---|---|---|---|---|
| 121 | X1-CH2CH2CH2-OMe | X2-C(O)-CH2CH2-Ph | Me2N-CH2CH2CH2-C(O)-X3 | A1, B2 | 0.86 | 459.5 |
| 122 | X1-CH2CH2-CH(CH3)2 | X2-O-C(O)-O-CH2-CH(CH3)2 | 3,5-(CF3)2-C6H3-CH2CH2-C(O)-X3 | A1, B1 | 2.03 | 580.5 |
| 123 | X1-CH2CH2-Ph | X2-C(O)-CH2CH2-Ph | H2N-CH2CH2CH2CH2CH2-C(O)-X3 | A1, B1 | 1.16 | 491.5 |
| 124 | X1-CH2CH2-CH(CH3)2 | X2-C(O)-CH2CH2-Ph | 3,5-(CF3)2-C6H3-CH2CH2-C(O)-X3 | A1, B1 | 2.07 | 612.5 |
| 125 | X1-CH2CH2-CH(CH3)2 | X2-C(O)-NH-CH2-Ph | Me2N-CH2CH2CH2-C(O)-X3 | A3, B1 | 1.09 | 458.5 |

TABLE 4-continued

Representative Compounds of Structure Type (III")

(III")

| Cpd | R1 | R2 | R3 | Method | LC RT | M+H+ |
|---|---|---|---|---|---|---|
| 126 | phenethyl (X1) | 2-(methylsulfonyl)ethyl carbonate (X2) | isobutyl carbonate (X3) | A2, B2 | 1.42 | 496.4 |
| 127 | isopentyl (X1) | 3-[3,5-bis(trifluoromethyl)phenyl]propanoyl (X2) | 5-chloro-1,3-dimethyl-1H-pyrazole-4-sulfonyl (X3) | A1, B4 | 1.91 | 672.4 |
| 128 | 3-methoxypropyl (X1) | 3-[3,5-bis(trifluoromethyl)phenyl]propanoyl (X2) | 3-phenylpropanoyl (X3) | A1, B1 | 1.79 | 614.4 |
| 129 | 2-(3,4-dimethoxyphenyl)ethyl (X1) | benzyl carbonate (X2) | 3-[3,5-bis(trifluoromethyl)phenyl]propanoyl (X3) | A2, B1 | 1.91 | 708.4 |

TABLE 4-continued

Representative Compounds of Structure Type (III'')

(III'')

| Cpd | R1 | R2 | R3 | Method | LC RT | M+H+ |
|---|---|---|---|---|---|---|
| 130 | X₁–(CH₂)₆–N(CH₃)₂ | 3,5-bis(trifluoromethyl)phenyl-CH₂CH₂C(O)–X₂ | Ph-CH₂CH₂C(O)–X₃ | A1, B1 | 1.42 | 669.5 |
| 131 | (CH₃)₂N–(CH₂)₆–X₁ | CH₃N(–(CH₂)₃C(O)–X₂) | 4-O₂N-C₆H₄-CH₂-O-C(O)–X₃ | A1, B2 | 0.17 | 561.5 |
| 132 | (CH₃)₂N–(CH₂)₆–X₁ | 3,5-bis(trifluoromethyl)phenyl-CH₂CH₂C(O)–X₂ | H₂N–(CH₂)₅–C(O)–X₃ | A1, B1 | 1.06 | 650.7 |
| 133 | (CH₃)₂CHCH₂CH₂–X₁ | CH₃N(–(CH₂)₃C(O)–X₂) | CH₃N(–(CH₂)₃C(O)–X₃) | A1, B1 | 0.17 | 438.6 |
| 134 | Ph-CH₂CH₂–X₁ | Ph-CH₂-O-C(O)–X₂ | H₂N–(CH₂)₅–C(O)–X₃ | A2, B1 | 1.09 | 493.4 |
| 135 | (CH₃)₂CHCH₂CH₂–X₁ | Ph-CH₂-O-C(O)–X₂ | H₂N–(CH₂)₅–C(O)–X₃ | A2, B1 | 1.1 | 459.4 |

Example 5

Synthesis of Representative Helix Mimetic

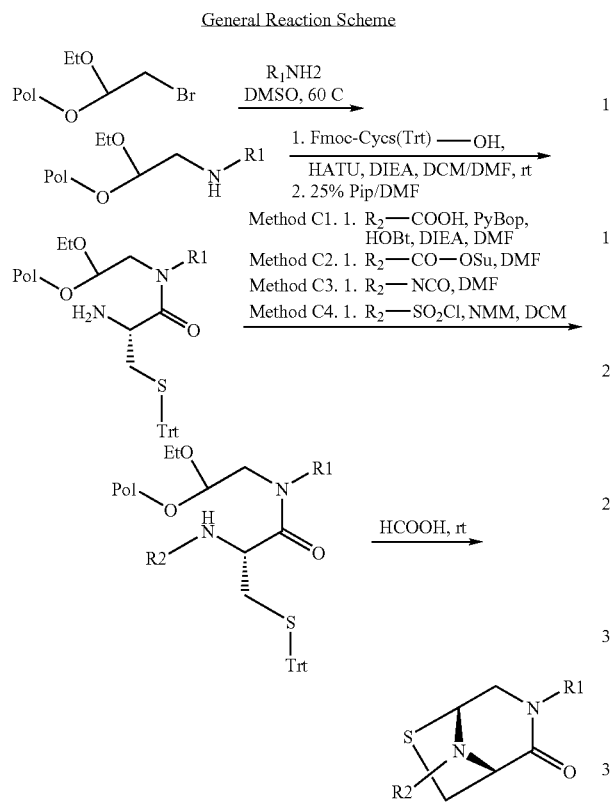

Commercially available 2-bromo-1-ethoxy-1-oxy-polystyrene resin (Pol-O—CH(OEt)-CH2—Br) (Advanced ChemTech) was suspended in DMSO to which an amine, $R_1NH_2$, (10 equivalents) was added. The resulting mixture was mechanically stirred using an overhead stirrer and heated to 60° C. After 24 h, the resin was filtered and washed sequentially with DMSO, DMF, MeOH, DMF, MeOH, and Et$_2$O then dried in vacuo. The substitution of the resin was determined spectroscopically by the Fmoc release method.

The secondary amine resin (Pol-O—CH(OEt)-CH$_2$—NHR$_1$) was contacted with a 0.05 N solution of α-Fmoc-S-Trt-Cystein (Fmoc-Cys(Trt)-OH), HATU and DIEA in DMF (4 equivalents). The resulting mixture was agitated for 2 h then tested against chloranil/acetaldehyde for complete reaction. Upon a negative chloranil test, the resin was filtered, sequentially washed with DMF, MeOH, DMF and MeOH. The Fmoc was deprotected by contacting the resin with 25% piperidine/DMF at room temperature. Following 1 h, the resin was drained, and washed sequentially with DMP, MeOH, DMF, MeOH and Et$_2$O and dried in vacuo.

Method C1

The deprotected resin (Pol-O—CH(OEt)-CH$_2$—NR$_1$—C(=O)—CH(CH$_2$S—Trt)—NH$_2$) was contacted with carboxylic acid (R$_2$CO$_2$H) and treated as previously described.

Method C2

The deprotected resin (Pol-O—CH(OEt)-CH$_2$—NR$_1$—C(=O)—CH(CH$_2$S—Trt)—NH$_2$) was contacted with N-hydroxysuccinimyl carbonate (R$_2$CO$_2$Su) and treated as previously described.

Method C3

The deprotected resin (Pol-O—CH(OEt)-CH$_2$—NR$_1$—C(=O)—CH(CH$_2$S—Trt)—NH$_2$) was contacted with isocyanate (R$_2$NCO) and treated as previously described.

Method C4

The deprotected resin (Pol-O—CH(OEt)-CH$_2$—NR$_1$—C(=O)—CH(CH$_2$S—Trt)—NH$_2$) was contacted with sulphonyl chloride (R$_2$SO$_2$Cl) and treated as previously described.

The resin resulting from Methods C1-C4 was swelled with DCM then contacted with glacial formic acid (approximately 2 mL/50 mg resin) for 14 h. The resulting solution was drained and the resin washed with formic acid (0.5 mL/50 mg resin). The combined solutions were evaporated in vacuo. The residue was dissolved in acetic acid, frozen to −76° C. and lyophilized.

Example 6

Synthesis of Representative Helix Mimetic

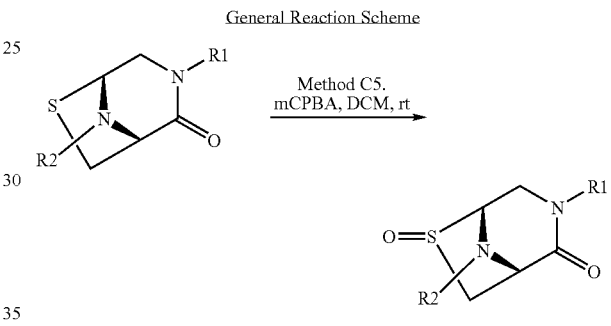

Compound products from Example 5 were dissolved in DCM to which one equivalent of mCPBA was added. The resulting solution was stirred for 10 minutes at room temperature then passed through neutral Al$_2$O$_3$. The product was eluted with 5% MeOH in DCM.

Example 7

Synthesis of Representative Helix Mimetic

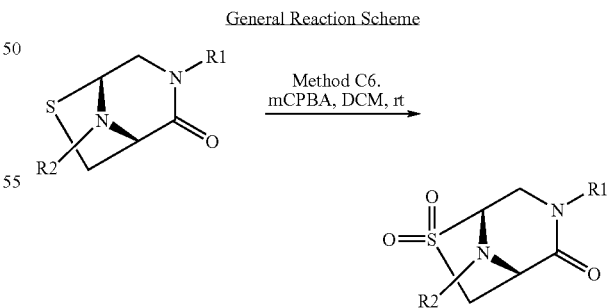

Compound products from Example 5 were dissolved in DCM to which an excess of mCPBA (3 to 5 eq.) was added. The resulting mixture was stirred for 1 h at r.t. and then stored overnight at −20° C. The resulting solution was filtered through a column of neutral Al$_2$O$_3$ eluting with 5% MeOH in DCM to obtain the product.

Example 8

Synthesis of Representative Helix Mimetic

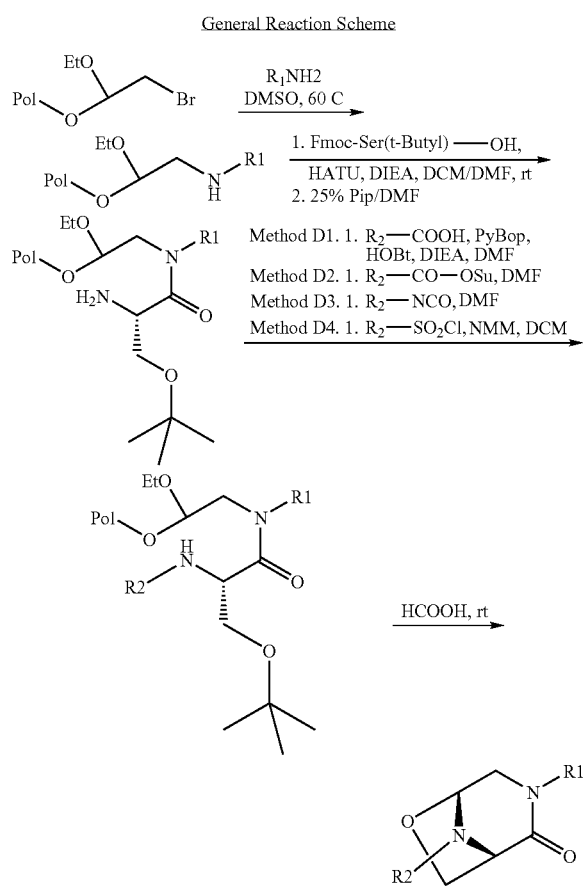

Commercially available 2-bromo-1-ethoxy-1-oxy-polystyrene resin (Pol-O—CH(OEt)—CH2—Br) (Advanced ChemTech) was suspended in DMSO to which an amine, $R_1NH_2$, (10 equivalents) was added. The resulting mixture was mechanically stirred using an overhead stirrer and heated to 60° C. After 24 h, the resin was filtered and washed sequentially with DMSO, DMF, MeOH, DMF, MeOH, and $Et_2O$ then dried in vacuo. The substitution of the resin was determined spectroscopically by the Fmoc release method.

The secondary amine resin (Pol-O—CH(OEt)-$CH_2$—$NHR_1$) was contacted with a 0.05 N solution of α-Fmoc-O-tert-Butyl-Serine (Fmoc-Ser(t-Butyl)-OH), HATU and DIEA in DMF (4 equivalents). The resulting mixture was agitated for 2 h then tested against chloranil/acetaldehyde for complete reaction. Upon a negative chloranil test, the resin was filtered, sequentially washed with DMF, MeOH, DMF and MeOH. The Fmoc was deprotected by contacting the resin with 25% piperidine/DMF at room temperature. Following 1 h, the resin was drained, and washed sequentially with DMF, MeOH, DMF, MeOH and $Et_2O$ and dried in vacuo.

Method D1

The deprotected resin (Pol-O—CH(OEt)-$CH_2$—$NR_1$—C(=O)—CH($CH_2$O-tButyl)-$NH_2$) was contacted with carboxylic acid ($R_2CO_2H$) and treated as previously described.

Method D2

The deprotected resin (Pol-O—CH(OEt)-$CH_2$—$NR_1$—C(=O)—CH($CH_2$O-tButyl)-$NH_2$) was contacted with N-hydroxysuccinimyl carbonate ($R_2CO_2Su$) and treated as previously described.

Method D3

The deprotected resin (Pol-O—CH(OEt)-$CH_2$—$NR_1$—C(=O)—CH($CH_2$O-tButyl)-$NH_2$) was contacted with isocyanate ($R_2NCO$) and treated as previously described.

Method D4

The deprotected resin (Pol-O—CH(OEt)-$CH_2$—$NR_1$—C(=O)—CH($CH_2$O-tButyl)-$NH_2$) was contacted with sulphonyl chloride ($R_2SO_2Cl$) and treated as previously described.

The resin resulting from Method D1-D4 was swelled with DCM then contacted with glacial formic acid (approximately 2 mL/50 mg resin) for 14 h. The resulting solution was drained and the resin washed with formic acid (0.5 mL/50 mg resin). The combined solutions were evaporated in vacuo. The residue was dissolved in acetic acid, frozen to −76° C. and lyopholized.

Example 9

Synthesis of Representative Helix Mimetic

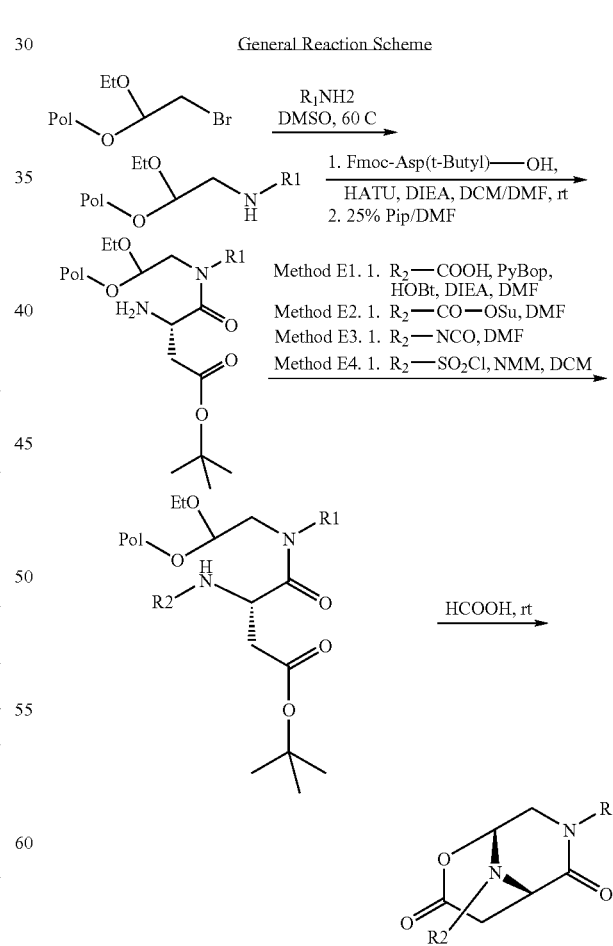

Commercially available 2-bromo-1-ethoxy-1-oxy-polystyrene resin (Pol-O—CH(OEt)—CH2—Br) (Advanced ChemTech) was suspended in DMSO to which an amine, $R_1NH_2$, (10 equivalents) was added. The resulting mixture was mechanically stirred using an overhead stirrer and heated to 60° C. After 24 h, the resin was filtered and washed sequentially with DMSO, DMF, MeOH, DMF, MeOH, and $Et_2O$ then dried in vacuo. The substitution of the resin was determined spectroscopically by the Fmoc release method.

The secondary amine resin (Pol-O—CH(OEt)-$CH_2$—$NHR_1$) was contacted with a 0.05 N solution of α-Fmoc-O-tert-Butyl-Aspartic Acid (Fmoc-Asp(t-Butyl)-OH), HATU and DIEA in DMF (4 equivalents). The resulting mixture was agitated for 2 h then tested against chloranil/acetaldehyde for complete reaction. Upon a negative chloranil test, the resin was filtered, sequentially washed with DMF, MeOH, DMF and MeOH. The Fmoc was deprotected by contacting the resin with 25% piperidine/DMF at room temperature. Following 1 h, the resin was drained, and washed sequentially with DMF, MeOH, DMF, MeOH and $Et_2O$ and dried in vacuo.

Method E1

The deprotected resin (Pol-O—CH(OEt)-$CH_2$—$NR_1$—C(=O)—CH($CH_2CO_2$-tButyl)-$NH_2$) was contacted with carboxylic acid ($R_2CO_2H$) and treated as previously described.

Method E2

The deprotected resin (Pol-O—CH(OEt)-$CH_2$—$NR_1$—C(=O)—CH($CH_2CO_2$-tButyl)-$NH_2$) was contacted with N-hydroxysuccinimyl carbonate ($R_2CO_2Su$) and treated as previously described.

Method E3

The deprotected resin (Pol-O—CH(OEt)-$CH_2$—$NR_1$—C(=O)—CH($CH_2CO_2$-tButyl)-$NH_2$) was contacted with isocyanate ($R_2NCO$) and treated as previously described.

Method E4

The deprotected resin (Pol-O—CH(OEt)-$CH_2$—$NR_1$—C(=O)—CH($CH_2CO_2$-tButyl)-$NH_2$) was contacted with sulphonyl chloride ($R_2SO_2Cl$) and treated as previously described.

The resin resulting from Method E1-E4 was swelled with DCM then contacted with glacial formic acid (approximately 2 mL/50 mg resin) for 14 h. The resulting solution was drained and the resin washed with formic acid (0.5 mL/50 mg resin). The combined solutions were evaporated in vacuo. The residue was dissolved in acetic acid, frozen to −76° C. and lyopholized.

Example 10

Synthesis of Representative Helix Mimetic

The representative compounds listed in Table 5 were synthesized according to the above procedures.

TABLE 5

Representative Compounds of Structure Type (IV''-VIII'')

| Cpd | R1 | R2 | Z | Method | LC RT | M + H⁺ |
|---|---|---|---|---|---|---|
| 136 | 4-fluorobenzyl ($X_1$) | phenethyl-NH-C(=O)-$X_2$ | S—$X_3$ / $X_3$ | C3 | 1.98 | 400.4 |
| 137 | morpholinoethyl ($X_1$) | O=S(=O)(phenyl)-$X_2$ | S—$X_3$ / $X_3$ | C4 | 1 | 398.4 |
| 138 | morpholinoethyl ($X_1$) | benzyl-O-C(=O)-$X_2$ | S—$X_3$ / $X_3$ | C2 | 1.15 | 392.4 |
| 139 | morpholinoethyl ($X_1$) | phenylpropanoyl-$X_2$ | S—$X_3$ / $X_3$ | C1 | 1.08 | 390.4 |

TABLE 5-continued
Representative Compounds of Structure Type (IV''-VIII'')
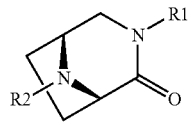
(IV''-VIII'')
| Cpd | R1 | R2 | Z | Method | LC RT | M + H⁺ |
|---|---|---|---|---|---|---|
| 140 | 4-F-benzyl-X₁ | PhSO₂-X₂ | X₃-S-X₃ | C4 | 2.02 | 393.4 |
| 141 | 4-F-benzyl-X₁ | PhCH₂OC(O)-X₂ | X₃-S-X₃ | C2 | 2.18 | 387.4 |
| 142 | 4-F-benzyl-X₁ | PhCH₂CH₂C(O)-X₂ | X₃-S-X₃ | C1 | 2.05 | 385.4 |
| 143 | 4-F-benzyl-X₁ | 4-MeO-C₆H₄-SO₂-X₂ | X₃-S-X₃ | C4 | 2.14 | 423.36 |
| 144 | 4-F-benzyl-X₁ | 4-MeO-C₆H₄-SO₂-X₂ | X₃-S(O)-X₃ | C4, C5 | 1.78 | 439.3 |
| 145 | 4-F-benzyl-X₁ | PhSO₂-X₂ | X₃-S(O)-X₃ | C4, C5 | 1.78 | 409.3 |
| 146 | 4-F-benzyl-X₁ | PhSO₂-X₂ | X₃-SO₂-X₃ | C4, C6 | 1.99 | 425.3 |

TABLE 5-continued
Representative Compounds of Structure Type (IV″-VIII″)
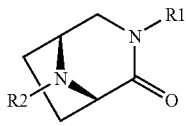
(IV″-VIII″)
| Cpd | R1 | R2 | Z | Method | LC RT | M + H+ |
|---|---|---|---|---|---|---|
| 147 | 4-F-C6H4-CH2-X1 | 4-MeO-C6H4-SO2-X2 | X3-SO2-X3 | C4, C6 | 2.14 | 455.3 |
| 148 | 4-F-C6H4-CH2-X1 | C6H5-SO2-X2 | X3-O-X3 | D4 | 1.92 | 377.2 |
| 149 | 4-F-C6H4-CH2-X1 | C6H5-CH2-CH2-C(O)-X2 | X3-O-C(O)-X3 | E1 | 1.88 | 397.4 |
| 150 | 4-F-C6H4-CH2-X1 | C6H5-CH2-O-C(O)-X2 | X3-O-C(O)-X3 | E2 | 1.97 | 399.4 |
| 151 | 4-F-C6H4-CH2-X1 | C6H5-NH-C(O)-X2 | X3-O-C(O)-X3 | E3 | 1.71 | 384.4 |
| 152 | 4-F-C6H4-CH2-X1 | C6H5-SO2-X2 | X3-O-C(O)-X3 | E4 | 1.77 | 405.3 |
| 153 | indol-3-yl-CH2CH2-X1 | -SO2-CH2CH2-O-C(O)-X2 | X3-S-X3 | C2 | 1.61 | 438.4 |

Example 11

Tachykinin Antagonism Assay of Representative Compounds

The compounds of this inventions are useful for antagonizing tachykinins, in particular substance P in the treatment of inflammatory diseases, central nervous system disorders, gastrointestinal disorders, pain or migraine and asthma in a mammal in need of such treatment. This activity can be demonstrated by the following assay.

An assay measuring the ability of Compounds 1-153 to antagonize binding of substance P peptide to its receptor neurokinin-1 was performed. Substance P is known to act upon cells via the mobilization of calcium (Bordey et al., *Glia* 11: 277-283, 1994). The compounds were assessed for their ability to inhibit the action of Substance P with the use of a Fluorescent Imaging Plate Reader (FLIPR) from Molecular Devices (Shroeder et al., *J. Biomol. Screening* 1: 75-80, 1996; U.S. Pat. Nos. 5,112,134; 4,968,148). U373 MG cells, which endogenously express the neurokinin-1 receptor for Substance P, were obtained from the American Type Culture Collection and grown to confluence in 96-well plates in modified Eagle's minimum essential medium (MEM) with 10% fetal bovine serum, 1 mM sodium pyruvate, 2 mM L-glutamine, and 1 mM non-essential amino acids in a humidified incubator at 37 C and 5% $CO_2$/95% filtered air. The cells were stained with Calcium Indicator dye from Molecular Devices for thirty minutes at room temperature; compounds were added to the cells, and the cells were further incubated for twenty minutes. This dye is similar to Fluo-3, Fluo-4, and Calcium Green dyes used by other researchers (Lin et al., *Biotechniques* 26: 318-326, 1999) in that it increases in fluorescence in the presence of calcium; the Molecular Devices version is preferable because the cells need not be washed following staining with the dye. Dye was made fresh on the day of the assay and included 2.5 mM probenecid, an anion exchange inhibitor which helps to keep the dye retained by the cells. Substance P was added in Hank's salt solution with 1% BSA to give a final concentration of 1 nM and the resultant change in fluorescence intensity was monitored for thirty seconds with an excitation wavelength of 480 nm and an emission of 515 nm. Some wells were maintained as controls which were not incubated with any compound, and the peak fluorescence readings resulting from the wells which received compounds were compared to these control wells in order to determine the degree of inhibition.

Preferably, the compounds of this invention have an inhibition value of better than or equal to 90% at 50 µM concentration in this assay. To this end, preferred compounds of this invention are compounds 2, 5, 8, 10, 26-30, 32, 33, 37, 39, 42, 45, 50, 53, 56, 58, 60-62, 64-66, 68, 71, 72, 76, 78, 79, 81, 82, 84, 86, 89, 90, 92, 94, 97, 98, 100, 102, 104, 108-112, 115, 121, 122, 128, 129, 131-135 and 153. As such, the compounds of this invention effectively inhibit binding of substance P peptide to its receptor neurokinin-1 and are effective in the treatment of inflammatory diseases and central nervous system disorders.

It will be appreciated that, although specific embodiments of the invention have been described herein for the purposes of illustration, various modifications may be made without departing from the spirit and scope of the invention. Accordingly, the invention is not limited except by the appended claims.

What is claimed is:

1. A fused bicyclo compound having the structure:

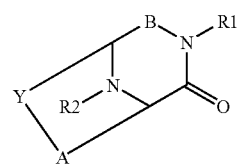

or pharmaceutically acceptable salt or stereoisomer thereof, wherein
Y is $SO_2$—, —SO— or —S—;
A is —$(CR_4R_{4a})_m$—;
B is —$(CR_5R_{5a})_n$—;
m is 1;
n is 1;
$R_4$ and $R_5$ are, at each occurrence, the same or different and independently an amino acid side chain moiety or an amino acid side chain derivative;
$R_{4a}$ and $R_{5a}$ are, at each occurrence, the same or different and independently hydrogen, hydroxy, —COOH, —$CONH_2$, —$R_6$, —$OR_6$, —$COOR_6$, —$COR_6$ or —$CONHR_6$;
$R_6$ is a lower alkyl optionally substituted with halogen or hydroxy;
$R_2$ is -Z-(amino acid side chain moiety) or -Z-(amino acid side chain derivative), where Z is a direct bond or —C(=O)—, —C(=O)O—, —C(=O)NH—, —C(=NH)—, —$SO_2$— or —$P(O)_{2,3}$—; and
$R_1$ is independently selected from a solid support, an amino acid side chain moiety, an amino acid side chain derivative, a peptide, a peptide derivative, a protein, -Z-(amino acid side chain moiety) or -Z-(amino acid side chain derivative), wherein Z is a direct bond or —C(=O)—, —C(=O)O—, —C(=O)NH—, —C(=NH)—, —$SO_2$— or —$P(O)_{2,3}$—;
wherein any two adjacent CH groups or adjacent NH and CH groups of the fused bicyclo compound optionally form a double bond;
and with the provisos that:
(a) when Y is —S— or —SO—, $R_1$ is not hydrogen; and
(b) when Y is —S— and m is 1, $R_4$ and $R_{4a}$ are not both methyl when $R_1$ is —C(=O)W, where W is phenyl, benzyl, —$CH_2O$(phenyl) or —OC(=O)(benzyl).

2. The compound of claim 1 wherein Y is —$SO_2$— and having the structure:

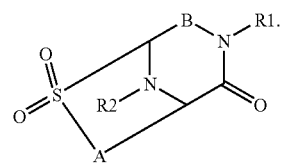

3. The compound of claim 2 wherein all occurrences of R$_4$, R$_{4a}$, R$_5$ and R$_{5a}$ are hydrogen, and having the structure:

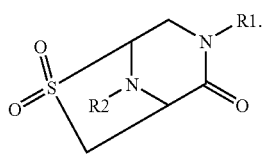

4. The compound of claim 1 wherein Y is —SO— and having the structure:

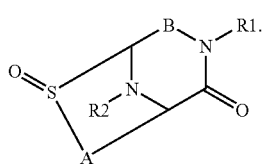

5. The compound of claim 4 wherein all occurrences of R$_4$, R$_{4a}$, R$_5$ and R$_{5a}$ are hydrogen, and-having the structure:

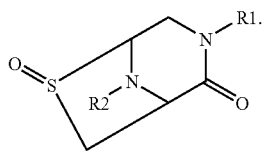

6. The compound of claim 1 wherein Y is —S— and having the structure:

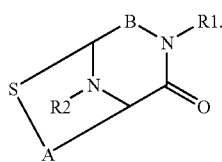

7. The compound of claim 6 wherein all occurrences of R$_4$, R$_{4a}$, R$_5$ and R$_{5a}$ are hydrogen, and-having the structure:

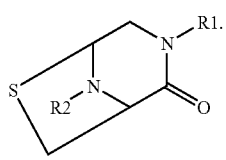

8. A pharmaceutical composition comprising a compound of claim 1 and a pharmaceutically acceptable carrier.

9. A library of compounds comprising a plurality of library members, wherein at least one library member is a compound of claim 1.

10. A method for identifying a biologically active compound, comprising screening the library of compounds of claim 9 for biological activity.

11. The compound of claim 7 having the structure:

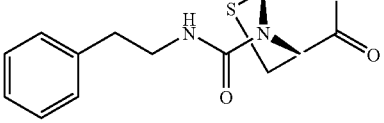

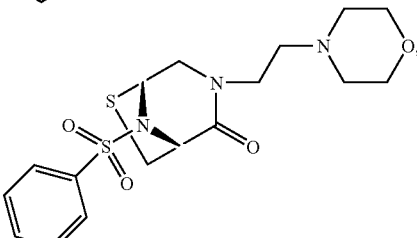

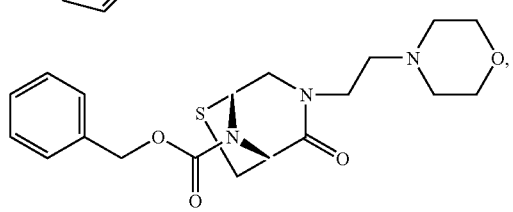

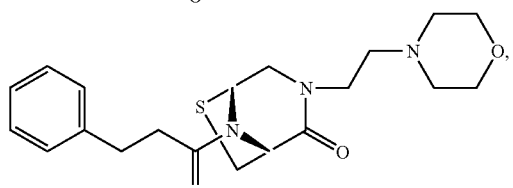

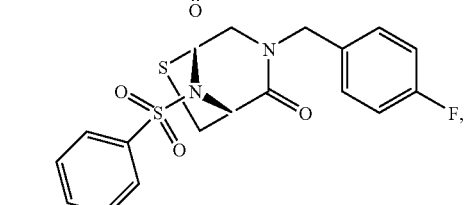

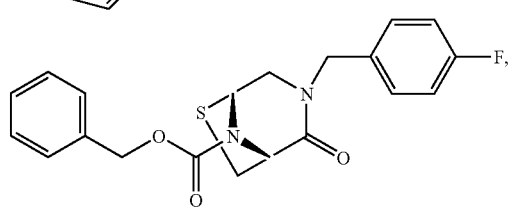

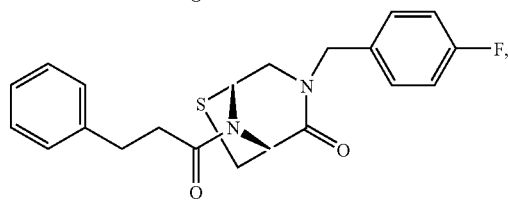

-continued
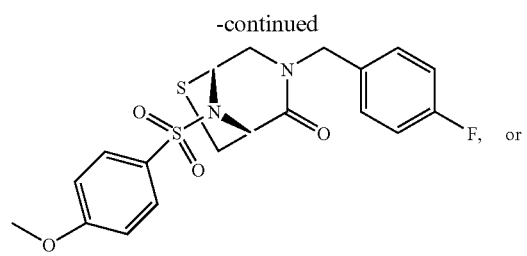
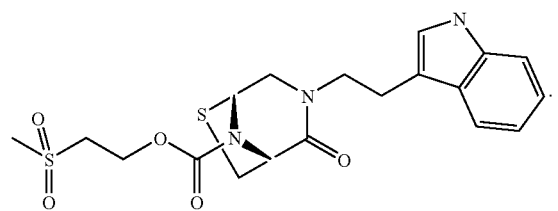
12. The compound of claim 4 having the structure:
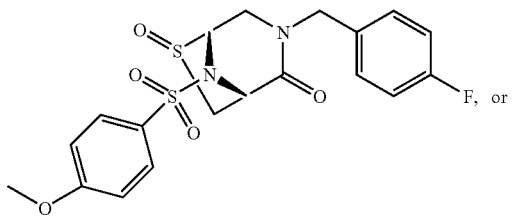
-continued
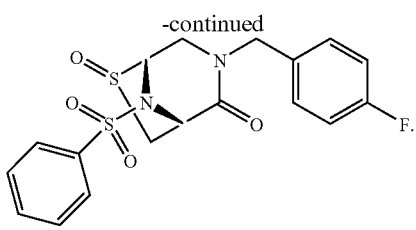
13. The compound of claim 2 having the structure:
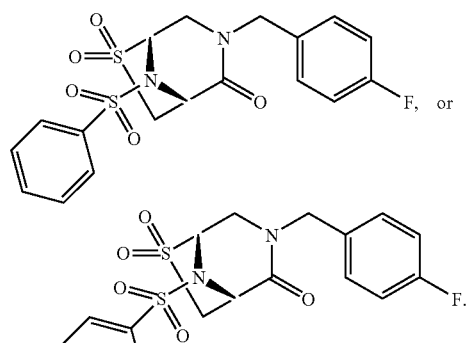
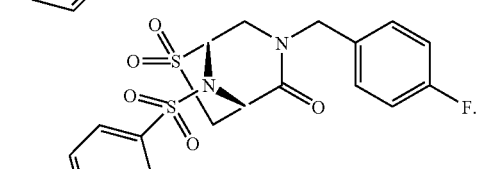
* * * * *